United States Patent
Hofmann et al.

(10) Patent No.: US 11,793,808 B2
(45) Date of Patent: Oct. 24, 2023

(54) COMPOSITIONS OF CLOFAZIMINE, COMBINATIONS COMPRISING THEM, PROCESSES FOR THEIR PREPARATION, USES AND METHODS COMPRISING THEM

(71) Applicant: MannKind Corporation, Westlake Villiage, CA (US)

(72) Inventors: Thomas Hofmann, Doylestown, PA (US); Stefan Ufer, Raleigh, NC (US); Kevin Stapleton, Laguna Beach, CA (US)

(73) Assignee: MANNKIND CORP., Westlake Village, CA (US)

( * ) Notice: Subject to any disclaimer, the term of this patent is extended or adjusted under 35 U.S.C. 154(b) by 66 days.

(21) Appl. No.: 17/181,448

(22) Filed: Feb. 22, 2021

(65) Prior Publication Data

US 2022/0265647 A1 Aug. 25, 2022

(51) Int. Cl.
| | |
|---|---|
| *A61K 31/498* | (2006.01) |
| *A61K 9/10* | (2006.01) |
| *A61K 31/47* | (2006.01) |
| *A61K 47/02* | (2006.01) |
| *A61K 9/00* | (2006.01) |
| *A61K 47/26* | (2006.01) |

(52) U.S. Cl.
CPC ............ *A61K 31/498* (2013.01); *A61K 9/008* (2013.01); *A61K 9/10* (2013.01); *A61K 31/47* (2013.01); *A61K 47/02* (2013.01); *A61K 47/26* (2013.01)

(58) Field of Classification Search
CPC .................................................. A61K 31/498
See application file for complete search history.

(56) References Cited

U.S. PATENT DOCUMENTS

| | | | |
|---|---|---|---|
| 6,514,482 | B1 | 2/2003 | Bartus et al. |
| 8,940,683 | B2 | 1/2015 | Levitt |
| 9,844,548 | B2 | 12/2017 | Gonda et al. |
| 9,907,754 | B2 | 3/2018 | Farrow et al. |
| 9,987,227 | B2 | 6/2018 | Cipolla et al. |
| 10,328,216 | B2 | 6/2019 | Boeckl et al. |
| 10,392,388 | B2 | 8/2019 | Ong et al. |
| 10,500,159 | B2 | 12/2019 | Amoro et al. |
| 10,550,389 | B2 | 2/2020 | Levitt |
| 10,624,893 | B2 | 4/2020 | Ballell Pages et al. |
| 10,905,660 | B2 | 2/2021 | O'Neil |
| 2001/0046526 | A1 | 11/2001 | Greenfelder |
| 2008/0038363 | A1 | 2/2008 | Zaffaroni et al. |
| 2009/0162441 | A1 | 6/2009 | Bartus et al. |
| 2009/0269396 | A1 | 11/2009 | Cipolla et al. |
| 2009/0312380 | A1 | 12/2009 | Becker |
| 2010/0028428 | A1 | 2/2010 | Hegyi et al. |
| 2010/0258118 | A1 | 10/2010 | Morton |
| 2014/0220091 | A1 | 8/2014 | Tofail et al. |
| 2016/0039823 | A1 | 2/2016 | Ong et al. |
| 2016/0207969 | A1 | 7/2016 | Lee et al. |
| 2016/0220710 | A1 | 8/2016 | Keswani et al. |
| 2016/0251380 | A1 | 9/2016 | Alley et al. |
| 2017/0056345 | A1 | 3/2017 | Timmins et al. |
| 2017/0209530 | A1 | 7/2017 | Heng et al. |
| 2017/0252446 | A1 | 9/2017 | Voigt et al. |
| 2017/0333427 | A1 | 11/2017 | Ho et al. |
| 2017/0348254 | A1 | 12/2017 | O'Neil |
| 2018/0000810 | A1 | 1/2018 | Gupta et al. |
| 2018/0250299 | A1 | 9/2018 | Kalman |
| 2019/0030026 | A1 | 1/2019 | Ho et al. |
| 2019/0175501 | A1 | 6/2019 | O'Neil |
| 2019/0262472 | A1 | 8/2019 | Hudson et al. |
| 2019/0282502 | A1 | 9/2019 | Boeckl et al. |
| 2019/0307760 | A1 | 10/2019 | Reiling et al. |
| 2019/0350928 | A1 | 11/2019 | Sanyal et al. |
| 2020/0009116 | A1 | 1/2020 | Borody |
| 2020/0009143 | A1 | 1/2020 | Timmins et al. |
| 2020/0046650 | A1 | 2/2020 | Baker et al. |
| 2020/0069588 | A1 | 3/2020 | Zhou et al. |
| 2020/0297626 | A1 | 9/2020 | Smyth et al. |
| 2020/0368312 | A1 | 11/2020 | Heckler et al. |
| 2021/0085620 | A1 | 3/2021 | Andries et al. |

(Continued)

FOREIGN PATENT DOCUMENTS

| | | |
|---|---|---|
| AU | 2012238199 A1 | 10/2012 |
| AU | 2017200228 B2 | 2/2017 |
| IN | 202017013676 A | 8/2020 |

(Continued)

OTHER PUBLICATIONS

Maartens et al., "Pharmacokinetic interaction between bedaquiline and clofazimine in patients with drug-resistant tuberculosis", Int J Tuberc Lung Dis. Jan. 1, 2018;22(1): pp. 26-30.
Martiniano et al., "Safety and Effectiveness of Clofazimine for Primary and Refractory Nontuberculous Mycobacterial Infection", Chest Infections, Oct. 2017; 152(4): pp. 800-809.
Aznar et al., "Safety and effectiveness of clofazimine in nontuberculous mycobacterial lung disease", Canadian Journal of Respiratory, Critical Care, and Sleep Medicine, vol. 2, 2018, Issue 2, pages.
Bald et al., "Targeting Energy Metabolism in Mycobacterium tuberculosis, a New Paradigm in Antimycobacterial Drug Discovery", mBio. Apr. 11, 2017;8(2): pp. 1-11.

(Continued)

*Primary Examiner* — John S Kenyon

(57) ABSTRACT

The present invention relates to pharmaceutical compositions for inhalation comprising a therapeutically effective dose of clofazimine wherein the clofazimine is provided in the form of a suspension, and processes for their preparation. Furthermore, the present invention provides pharmaceutical combinations comprising clofazimine in the form of an aerosol for pulmonary inhalation. The combinations and compositions provided by the present invention may be used in the treatment and/or prophylaxis of pulmonary infections caused by mycobacteria and other gram-positive bacteria, and of pulmonary fungal infections.

25 Claims, No Drawings

(56) References Cited

U.S. PATENT DOCUMENTS

2021/0100786 A1    4/2021    Malhotra et al.

FOREIGN PATENT DOCUMENTS

| WO | 2012073025 | A1 | | 6/2012 | |
|---|---|---|---|---|---|
| WO | 2017127641 | A1 | | 7/2017 | |
| WO | 2018217800 | A1 | | 11/2018 | |
| WO | 2019070693 | A1 | | 4/2019 | |
| WO | 2020023614 | A1 | | 1/2020 | |
| WO | 2020040818 | A1 | | 2/2020 | |
| WO | WO-2020040818 | A1 | * | 2/2020 | ............. A61K 31/47 |
| WO | 2020106787 | A1 | | 5/2020 | |
| WO | 2020144197 | A1 | | 7/2020 | |
| WO | 2020169747 | A1 | | 8/2020 | |
| WO | 2020172594 | A1 | | 8/2020 | |

OTHER PUBLICATIONS

Brunaugh et al., "Excipient-Free Pulmonary Delivery and Macrophage Targeting of Clofazimine via Air Jet Micronization" Nov. 6, 2017;14(11):4019-4031.
Pilcer et al. "Formulation strategy and use of excipients in pulmonary drug delivery" Int J Pharm. Jun. 15, 2010;392(1-2):1-19.
Murashov et al. "Synthesis and Characterization of a Biomimetic Formulation of Clofazimine Hydrochloride Microcrystals for Parenteral Administration" Pharmaceutics, Nov. 17, 2018;10(4):238, pp. 1-14.
International Search Report dated Jun. 27, 2019 for International Application No. PCT/US2019/025538 filed on Apr. 3, 2019.
Adler-Shohet et al., "2277. Clofazimine for Treatment of *Mycobacterium abscessus* Infections in Children", Poster Abstracts, OFID, 2017, vol. 4, p. 675.
Ruth et al., "A bedaquiline/clofazimine combination regimen might add activity to the treatment of clinically relevant non-tuberculous mycobacteria", Journal of Antimicrobial Chemotherapy, Apr. 1, 2019;74(4),pp. 1-9.
Berry et al., "A New Series of Phenazines (Rimino-Compounds) With High Antituberculosis Activity", Nature, No. 4568, May 18, 1957, pp. 1013-1015.
Schwartz et al. "Activities of Dual Combinations of Antibiotics Against Multidrug-Resistant Nontuberculous Mycobacteria Recovered from Patients with Cystic Fibrosis", Disease, Microbial Drug Resistance, vol. 00, No. 00, 2017, pp. 1-7.
Barry et al., "Antituberculosis Activity in the Phenazine Series. Isomeric Pigments Obtained By Oxidation of 0-Phenylenediamine Derivatives", Laboratories of the Medical Research Council of Ireland, Trinity College, Dublin, Jun. 12, 2056, pp. 1089-1096.
Diacon et al., "Bactericidal Activity of Pyrazinamide and Clofazimine Alone and in Combinations with Pretomanid and Bedaquiline" Am J Respir Crit Care Med. Apr. 15, 2015;191(8), pp. 943-953.
Roy et al., "Evaluation of genotoxicity of clofazimine, an antileprosy drug, in mice in vivo. II. Micronucleus test in bone marrow and hepatocytes", Mutation Research, 241 (1990), pp. 169-173.
Shen et al., "High efficacy of clofazimine and its synergistic effect with amikacin against rapidly growing mycobacteria", Int J Antimicrob Agents. Apr. 2010;35(4), pp. 400-404.
Singh et al., "In vitro evaluation of a new drug combination against clinical isolates belonging to the *Mycobacterium abscessus* complex", Clin Microbiol Infect. Dec. 2014;20(12), pp. O124-O1127.
Ingen et al., "In Vitro Synergy between Clofazimine and Amikacin in Treatment of Nontuberculous Mycobacterial Disease", Antimicrobial Agents and Chemotherapy, Dec. 2012 vol. 56 No. 12, pp. 6324-6327.
Janulionis et al., "Lack of Activity of Orally Administered Clofazimine against Intracellular *Mycobacterium tuberculosis* In Whole-Blood Culture", Antimicrobial Agents and Chemotherapy, vol. 48, No. 8, Aug. 2004, pp. 3133-3135.

Yawalkar et al., "Lamprene ( Clofazimine) in Leprosy", Lepr Rev. Jun. 1979;50(2) pp. 135-144.
Cholo et al., "Mechanisms of action and therapeutic efficacies of the lipophilic antimycobacterial agents clofazimine and bedaquiline", Antimicrob Chemother 2017; 72: pp. 338-353.
Feng et al., "Metabolism of Clofazimine in Leprosy Patients", Drug Metab Dispos. Nov.-Dec. 1981;9(6):pp. 521-524.
Feng et al., "A New Urinary Metabolite of Clofazimine in Leprosy Patients", Drug Metab Dispos. May-Jun. 1982;10(3):pp. 286-288.
Yoon et al., "Phagocytosed Clofazimine Biocrystals can Modulate Innate Immune Signaling by Inhibiting TNFα and Boosting IL-1RA Secretion", Mol Pharm. Jul. 6, 2015; 12(7): pp. 1-22.
Mack R. Holdiness, "Clinical Pharmacokinetics of Clofazimine A Review", Clinical Pharmacokinetics 16: 1989, pp. 74-85.
Charles A. Peloquin, "Clinical Pharmacology of Clofazimine", Infectious Disease Pharmacokinetics Laboratory College of Pharmacy and The Emerging Pathogens Institute University of Florida.
Martiniano et al., "Clinical Significance of a First Positive Nontuberculous Mycobacteria Culture in Cystic Fibrosis", Ann Am Thorac Soc. Jan. 2014;11(1):36-44.
Yoon et al., "Clinical significance of QT-prolonging drug use in patients with MDR-TB or NTM disease", Int J Tuberc Lung Dis 21(9):996-1001.
Yoon et al., "Clofazimine Biocrystal Accumulation in Macrophages Upregulates Interleukin 1 Receptor Antagonist Production To Induce a Systemic Anti-Inflammatory State", Antimicrobial Agents and Chemotherapy, Jun. 2016 vol. 60 No. 6, pp. 3470-3479.
Wang et al., "Clofazimine for Treatment of Extensively Drug-Resistant Pulmonary Tuberculosis in China", Antimicrobial Agents and Chemotherapy, Apr. 2018 vol. 62 Issue 4 e02149-17, pp. 1-9.
Ferro et al., "Clofazimine Prevents the Regrowth of *Mycobacterium abscessus* and *Mycobacterium avium* Type Strains Exposed to Amikacin and Clarithromycin", Antimicrobial Agents and Chemotherapy, Feb. 2016 vol. 60 No. 2, pp. 1097-1105.
O'Driscoll et al., "Clofazimine", Analytical Profiles of Drug Substances and Excipients—vol. 21, 1992, pp. 75-108.
Sangana et al., "Evaluation of Clinical Drug Interaction Potential of Clofazimine Using Static and Dynamic Modeling Approaches", Drug Metab Dispos. Jan. 2018;46(1), pp. 26-32.
Das et al., "Evaluation of genotoxicity of clofazimine, an antileprosy drug, in mice in vivo. I. Chromosome analysis in bone marrow and spermatocytes", Mutation Research, 241 (1990), pp. 161-168.
Verma et al., "Inhaled Microparticles Containing Clofazimine Are Efficacious in Treatment of Experimental Tuberculosis in Mice", Antimicrobial Agents and Chemotherapy Journal, Feb. 2013, vol. 57, pp. 1050-1052.
Bannigan et al., "Investigation into the Solid and Solution Properties of Known and Novel Polymorphs of the Antimicrobial Molecule Clofazimine", Crystal Growth Design, Nov. 7, 2016, vol. 16, pp. 7240-7250.
International Preliminary Report on Patentability and Written Opinion dated May 10, 2022 for International Application No. PCT/US2020/058447 filed on Nov. 1, 2020.
International Preliminary Report on Patentability and Written Opinion dated Oct. 27, 2022 for International Application No. PCT/US2021/030155 filed on Apr. 30, 2021.
Banaschewski et al., "Clofazimine inhalation suspension for the aerosol treatment of pulmonary nontuberculous mycobacterial infections", Journal of Cystic Fibrosis, 2019, vol. 18, No. 5, pp. 714-720.
Peters et al., Preparation of a Clofazimine Nanosuspension for intravenous use and evaluation of its Therapeutic Efficacy in Murine *Mycobacterium avium* Infection, Journal of Antimicrobial Chemotherapy, vol. 45, Issue 1, Jan. 2000, pp. 77-83.
Japanese Notice of Reasons for Refusal dated Dec. 6, 2022 for JP Application No. 2021-510120 filed on Apr. 3, 2019.

* cited by examiner

COMPOSITIONS OF CLOFAZIMINE, COMBINATIONS COMPRISING THEM, PROCESSES FOR THEIR PREPARATION, USES AND METHODS COMPRISING THEM

This application is a national stage application of PCT/US2019/025538, filed Apr. 3, 2019, which claims the benefit of U.S. Provisional Application No. 62/722,048, filed Aug. 23, 2018, and also claims the benefit of U.S. Provisional Application No. 62/796,322, filed Jan. 25, 2019, the entirety of their contents of which are incorporated herein by reference.

FIELD OF THE INVENTION

The present invention relates to pharmaceutical compositions for inhalation comprising a therapeutically effective dose of clofazimine, wherein the clofazimine is provided in the form of a suspension; processes for their preparation; and uses and methods of treatment comprising them. Furthermore, the present invention provides pharmaceutical combinations comprising clofazimine in the form of an aerosol for pulmonary inhalation.

The combinations and compositions provided by the present invention may be used in the treatment and/or prophylaxis of pulmonary infections caused by mycobacteria and other gram-positive bacteria, and of pulmonary fungal infections.

BACKGROUND OF THE INVENTION

Clofazimine is an extremely hydrophobic riminophenazine antibiotic (Log P=7.66) with anti-mycobacterial and anti-inflammatory activities and was originally described in 1957. Its structural formula is as follows:

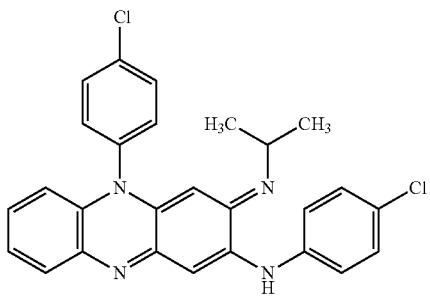 [SMILES: CC(C)/N=c1\cc2n(-c3ccc(Cl)cc3)c3ccccc3nc-2cc1Nc1ccc(Cl)cc1]

The exact mechanism through which clofazimine exerts its antimicrobial effect is unknown. However, it is known to bind preferentially to mycobacterial DNA, thereby inhibiting DNA replication and cell growth. Other suggested mechanisms of action include membrane damage/destabilization, generation of membrane-destabilizing lysophospholipids, interference of potassium transport, and/or intracellular redox cycling. While impressively active against *Mycobacterium tuberculosis* (MTB) in vitro, including multidrug-resistant strains, clofazimine, until recently, was generally considered to be ineffective in the treatment of pulmonary tuberculosis (see, for example, Cholo M et al., *J Antimicrob Chemother*, 2012 February, 67 (2):290-8).

Clofazimine is one of the three principal drugs recommended by the World Health Organization for the treatment of leprosy which is caused by *Mycobacterium leprae* and has been increasingly used for the treatment of other mycobacterial infections such as drug resistant tuberculosis and infections caused by nontuberculous mycobacteria (NTM) in recent years.

Clofazimine has been classified as a Biopharmaceutics Classification System (BCS) class II drug as it is practically insoluble in water and shows high membrane permeability.

To overcome the problems associated with poor oral absorption and poor bioavailability of drugs, various strategies have been applied such as micronization, nanonization, supercritical fluid re-crystallization, spray freeze drying into liquid, solid dispersions and solutions in optimizing oral dosage forms.

Being classified as a BCS class II drug, clofazimine is generally considered an ideal candidate for the formulation into solid dispersions for improvement of oral bioavailability (see, for example, Bhusnure et al. *IJRPC* 2014, 4 (4), 906-918).

In line with this, because of its lipophilicity, clofazimine is generally administered as a microcrystalline suspension in an oil-wax base to improve oral absorption. The absorption in humans after oral administration varies considerably (45-62%). Adverse effects of clofazimine are dose related and primarily affect the skin, eyes, gastrointestinal tract, and QT elongation Side effects include the development of reddish-brown discoloration of the skin and conjunctiva and are gradually reversible on cessation. They are the result of chronic systemic accumulation.

*Mycobacterium* is a genus *Actinobacteria*, with its own genus, *Mycobacteriaceae*. Mycobacteria have characteristic rod-like shapes and waxy outer coats.

As such, *Mycobacteria* can be divided into three groups:
- *Mycobacterium tuberculosis* complex—causative pathogen of tuberculosis
- *Mycobacterium leprae*—causative pathogen of leprosy
- Nontuberculous mycobacteria (NTM) which encompass all other mycobacteria that are not *M. tuberculosis* or *M. leprae*, including *Mycobacterium abscessus* complex (MABSC), *Mycobacterium avium* complex (MAC).

Tuberculosis (TB) is an infectious disease caused by *Mycobacterium tuberculosis* complex bacteria. As one of the oldest documented infectious agents in humans, TB remains a significant cause of mortality and morbidity worldwide, with an estimated 10.4 million new cases of TB infection, and 1.4 million people killed by active TB disease in 2015 (see, for example, World Health Organization (WHO) Global Tuberculosis Report 2016). In addition to the high prevalence and mortality rates, the incidence of multi-drug resistant tuberculosis (MDR-TB) is a growing concern, with 580,000 patients presenting with a drug-resistant TB infection in 2015. Co-morbidities, such as human immunodeficiency virus (HIV), complicate treatment, and were responsible for 1.2 million cases of TB in 2015.

To treat multi-drug resistant (MDR) infections, the WHO has recommended implementing a 9 to 12 month treatment regimen of second-line anti-TB drugs. These regimens, such as the 9 to 12 month Bangladesh regimen, treat MDR-TB with a combination of gatifloxacin, ethambutol, pyrazinamide, and clofazimine, which led to a relapse-free cure in 87.9% of patients (see, for example, Sotgiu, G, et al., "Applicability of the shorter 'Bangladesh regimen' in high multidrug-resistant tuberculosis settings", *International Journal of Infectious Diseases* (2017) 56 190-193).

Other studies investigating shortened TB treatments demonstrated that clofazimine had no clinical benefit after two weeks of oral administration (see, for example, Diacon, A. H., et al., "Bactericidal Activity of Pyrazinamide and Clofazimine Alone and in Combinations with Pretomanid and Bedaquiline", *American Journal of Respiratory and Critical Care Medicine* (2015), 191 (8), 943-953). The lack of activity was attributed to low bioavailability of the drug, as it was theorized to bind to circulating serum proteins with a high affinity. There, despite the fact that clofazimine has been empirically demonstrated to be effective for the treatment of MDR-TB, and extensively-drug resistant TB (XDR-TB), its poor bioavailability after systemic administration appears to limit its biological activity over short duration therapies (see, for example, Swanson, R. V., et al., "Pharmacokinetics and Pharmacodynamics of Clofazimine in a Mouse Model of Tuberculosis", *Antimicrobial Agents and Chemotherapy* (2015), 59 (6), 3042-3051).

It is known that treatment of lung infections with inhaled antibiotics results in higher drug concentrations in the lungs and reduced adverse effects compared to systemic delivery (see, for example, Touw, D. J., et al., "Inhalation of antibiotics in cystic fibrosis", *European Respiratory Journal* (1995), 8, 1594-1604), which result in increased biological activity and efficacy (see, for example, Hickey, A. J., "Inhaled drug treatment for tuberculosis: Past progress and future prospects", *Journal of Controlled Release*, (2016), 240, 127-134). In vivo mouse models have demonstrated that aerosolized administration of clofazimine shows significant improvement in bacilli clearance in TB-infection models compared to oral administration of clofazimine only 28 days after treatment initiation (see, for example, Verma, R. K., et al., "Inhaled microparticles containing clofazimine are efficacious in treatment of experimental Tuberculosis in Mice", *Antimicrobial Agents and Chemotherapy* (2013), 57 (2), 1050-1052). This improved efficacy over a short duration is likely due to the direct delivery of clofazimine to the site of infection in the lungs resulting in higher clofazimine concentration in the pulmonary macrophages within the tuberculosis granulomas.

Accordingly, the use of an aerosolized administration of clofazimine in patients with MDR TB, or XDR-TB infections should further improve patient treatment outcomes, and may shorten the duration of current treatment regimens.

The group of nontuberculous mycobacteria (NTM), formerly called atypical or ubiquitous mycobacteria, contains over 150 species. NTM can be found ubiquitously in nature and show a broad diversity. They can be detected in soil, ground and drinking water as well as in food like pasteurized milk or cheese. In general, NTM are considered to be less pathogenic. Nevertheless, they can cause severe illness in humans, especially in immune compromised persons or those who suffer from previous pulmonary diseases. Currently NTM are classified according to their growth rate and are divided into slow-growing (SGM) and rapid-growing (RGM) *mycobacteria*.

The slow growing *Mycobacterium avium* complex (MAC) comprises the species *Mycobacterium avium*, *Mycobacterium chimaera* and *Mycobacterium intracellulare* that are among the most important and most frequent pathogenic NTM. Just like *Mycobacterium kansasii, Mycobaceterium malmoense, Mycobacterium xenopi, Mycobacterium. simiae, Mycobacterium abscessus, Mycobacterium gordonae, Mycobacterium fortuitum*, and *Mycobacterium chelonae*, they mostly cause pulmonary infections. *Mycobacterium marinum* is responsible for skin and soft tissue infections like aquarium granuloma.

In particular, RGM cause serious, life-threatening chronic lung diseases and are responsible for disseminated and often fatal infections. Infections are typically caused by contaminated materials and invasive procedures involving catheters, non-sterile surgical procedures or injections and implantations of foreign bodies. Exposure to shower heads and Jacuzzis has also been reported as risks for infections. NTM typically cause opportunistic infections in patients with chronic pulmonary diseases such as chronic obstructive pulmonary disease (COPD), cystic fibrosis (CF), and other immune compromised patients.

In recent years, the rapidly growing (RGM) *Mycobacterium abscessus* group strains (*Mycobacterium abscessus* complex, MABSC) comprising the subspecies *Mycobacterium abscessus* subsp. *abscessus* (*M. a. abscessus*), *Mycobacterium abcessus bolletii*. and *Mycobacterium abscessus massiliense* have emerged as important human pathogens and are associated with significantly higher fatality rates than any other RGM.

*Mycobacterium abscessus* infection in CF patients are particularly problematic, as it results in enhanced pulmonary destruction and is often impossible to treat with failure rates as high as 60-66%. (see, for example, Obregon-Henao A et al, *Antimicrobial Agents and Chemotherapy*, November 2015, Vol 59, No 11, p. 6904-6912; Qvist, T., Pressler, T., Høiby, N. and Katzenstein, T L., "Shifting paradigms of nontuberculous mycobacteria in cystic fibrosis", *Respiratory Research* (2014), 15(1): pp. 41-47).

Human infection with NTM became of greater relevance with the emergence of the human acquired immune deficiency syndrome pandemic. Mycobacteria from *Mycobacterium avium* complex (MAC) were identified as the major cause of opportunistic infections in patients infected with the human immunodeficiency virus (HIV).

Several species of NTM are known to form biofilms. Biofilms are microcolonies of bacteria embedded in the extracellular matrix that provide stability and resistance to human immune mechanisms. In recent years, some species of NTM have been shown to form biofilms that enhance resistance to disinfectants and antimicrobial agents. Biofilm assembly proceeds through several phases, including reversible attachment, irreversible attachment, biofilm formation via bacterial aggregation, organization, and signaling, and finally dispersion. During this process, bacteria develop a matrix containing extracellular polymeric substances (EPS), such as polysaccharides, lipids and nucleic acids, to form a complex three-dimensional structure (see, for example, Sousa S. et al., *International Journal of Mycobacteriology* 4 (2015), 36-43). Specifically, mycobacterial EPS differ in nature from other biofilms, as mycobacteria do not produce exopolysaccharides (see, for example, Zambrano M M, Kolter R. Mycobacterial biofilms: a greasy way to hold it together. *Cell*. 2005). Mycobacterial biofilms vary between species, but can contain mycolic acids, glycopeptidolipids, mycolyl-diacylglycerols, lipooligosaccharides, lipopeptides, and extracellular DNA (Overview and original research from: Rose S J, Babrak L M, Bermudez L E (2015) *Mycobacterium avium* Possesses Extracellular DNA that Contributes to Biofilm Formation, Structural Integrity, and Tolerance to Antibiotics. PLoS ONE). The assembly in biofilms is known to enhance resistance to antimicrobial agents (see, for example, Faria S. et al., *Journal of Pathogens*, Vol 2015, Article ID 809014).

Delivery of aerosolized liposomal amikacin/inhaled amikacin solution nebulized by a jet nebulizer as a novel approach for treatment of NTM pulmonary infection has been suggested (Rose S. et al, 2014, PLoS ONE, Volume 9, Issue 9, e108703, and Olivier K. et al, Ann Am Thorac Soc Vol 11, No 1, pp. 30-35) as well as inhalation of anti-TB drugs dry powder microparticles for pulmonary delivery (Cholo M et al., *J Antimicrob Chemother*. 2012 February; 67

(2):290-8 and Fourie B. and Nettey O., 2015 Inhalation Magazine, Verma 2013 Antimicrob Agents Chemother).

Multiple combination regimens with inhaled amikacin following initial treatment with parenteral aminoglycosides, tigecycline and other promising oral antibiotics such as linezolid, delamanid, and bedaquiline, and surgical intervention in selected cases have shown promising results in the treatment of NTM lung disease (Lu Ryu et al., *Tuberc Respir Dis* 2016; 79:74-84). However, the increasing incidence and prevalence of NTM infections, in particular NTM lung disease and the limited treatment options necessitate the development of novel dosage forms/pharmaceutical formulation enhancing the bioavailability of the currently used antibiotics such as clofazimine. Inhalation may enhance efficacy and reduce adverse effects compared to oral and parenteral therapies.

Combinations of clofazimine and amikacin have been shown to act synergistically in vitro against both *Mycobacterium abscessus* and *Mycobacterium avium* (see, for example, van Ingen, J., et al., "In Vitro Synergy between Clofazimine and Amikacin in Treatment of Nontuberculous Mycobacterial Disease", *Antimicrobial Agents and Chemotherapy* 56 (12), 6324-6327 (2012)). Further, synergy has been shown with combinations of clofazimine and bedaquiline used against *Mycobacterium tuberculosis* (see, for example, Cokol, M. et al., "Efficient Measurement and factorization of high-order drug interactions in *Mycobacterium tuberculosis*", *Sciences Advances* 2017:3:e170881, 11 Oct. 2017). Synergy has also been shown for a clofazimine/bedaquiline combination against the nontuberculous bacterium *Mycobacterium abscessus* (Ruth, M. M. et al., "A Bedaquiline/Clofazimine Combination Regimen Might Add Activity to the Treatment of Clinically Relevant Non-Tuberculous Mycobacteria", *Journal of Antimicrobial Chemotherapy* (2019), doi.org/10.1093/jac/dky526).

Fungal pathogens have emerged as a leading cause of human mortality. Current estimates suggest death due to invasive fungal infections is on par with more well-known infectious diseases such as tuberculosis. *Candida albicans*, *Cryptococus neoformans*, and *Aspergillus fumigatus* represent the most prevalent fungal pathogens of humans. Each of these species is responsible for hundreds of thousands of infections annually with unacceptably high mortality rates due to poor diagnostics and limited treatment options. Clofazimine has been shown to exhibit efficacy as a combination agent against multiple fungi. (see, for example, Robbins, N., et al., "An Antifungal Combination Matrix Identifies a Rich Pool of Adjuvant Molecules that Enhance Drug Activity against Diverse Fungal Pathogens", *Cell Reports* 13, 1481-1492, Nov. 17, 2015). Fungi also play a role as commensals, colonizers and/or pathogens in cystic fibrosis (see, for example, Chotirmall, S. H. and McElvaney, N. G., "Fungi in the cystic fibrosis lung: Bystanders or pathogens?", *The International Journal of Biochemistry & Cell Biology* 52 (2014), 161-173.

The low solubility of clofazimine in water results in low oral bioavailability and high microbial resistance and also requires specific techniques to solubilise and stabilize the drug for formulation in liquid aqueous carriers such as for aerosolization by nebulizers in order to obtain lower lung deposition of the aerosol particles.

SUMMARY OF THE INVENTION

In an embodiment of the invention, a pharmaceutical composition is provided comprising:

(a) a therapeutically effective dose of clofazimine or a pharmaceutically acceptable derivative or salt thereof;
(b) a nonionic surfactant with an Hydrophilic-Lipophilic Balance value of greater than 10; and
(c) an aqueous liquid carrier selected from water, isotonic saline, buffered saline and aqueous electrolyte solutions wherein the clofazimine, or the pharmaceutically acceptable derivative or salt thereof, is provided in the form of particles in a suspension, and wherein the particles of clofazimine, or the pharmaceutically acceptable derivative or salt thereof, have a median size of less than 5 μm and a D90 of less than 6 μm.

In another embodiment of the invention, the particles of clofazimine, or the pharmaceutically acceptable derivative or salt thereof, have a mean size of less than 2 μm and a D90 of less than 3 μm.

In another embodiment of the invention a pharmaceutical composition is provided comprising:

(a) a therapeutically effective dose of clofazimine;
(b) a nonionic surfactant with an Hydrophilic-Lipophilic Balance value of greater than 10; and
(c) an aqueous liquid carrier selected from water, isotonic saline, buffered saline and aqueous electrolyte solutions wherein the clofazimine is provided in the form of particles in a suspension, and wherein the particles of clofazimine have a median size of less than 5 μm and a D90 of less than 6 μm.

In another embodiment of the invention the particles of clofazimine have a median size of less than 2 μm and a D90 of less than 3 μm.

The aerosolization of the compositions of the invention by an appropriate nebulizer provides significantly increased delivery of the aerosolized clofazimine into the lower lung (i.e. to the bronchi, bronchioli, and alveoli of the central and lower peripheral lungs), thereby substantially enhancing the therapeutic efficacy.

The inhalation device should, moreover, preferably be further adapted for localized pulmonary delivery of an aerosol having an optimal particle size distribution for homogenous deposition in the lower lung.

The invention therefore provides for an aerosol having aerosol particles of sizes that facilitate delivery to the alveoli and bronchiole. A suitable aerodynamic particle size for targeting the alveoli and bronchiole is between 1 and 5 μm. Particles larger than that are selectively deposited in the upper lungs, namely bronchi and trachea and in the mouth and throat, i.e. oropharyngeal area. Accordingly, the inhalation device is adapted to produce an aerosol having a mass median aerodynamic diameter (MMAD) in the range from about 1 to about 5 μm, and preferably in the range from about 1 to about 3 μm. In a further embodiment, the particle size distribution is narrow and has a geometric standard deviation (GSD) of less than about 2.5.

DETAILED DESCRIPTION OF THE INVENTION

The present invention is based on the unexpected discovery that by pulmonary aerosol administration of clofazimine in the form of a suspension, lower (i.e. deeper) lung deposition of the active agent can be achieved, thereby significantly increasing the bioavailability of the extremely hydrophobic BCS class II agent, which results in significantly increased therapeutic efficacy coupled with reduced systemic side effects.

In another aspect, this finding leads to the provision of an improved antibiotic therapy for infections caused by mycobacteria and gram-positive bacteria, in particular of pulmonary infections with NTM, such as opportunistic infections in CF, COPD and immune compromised patients such as HIV patients.

The present invention, moreover, aims at overcoming systemic side effects of established oral treatment regimens for pulmonary infections with gram positive bacteria, in particular TB and NTM infections of the lungs as well as at the reduction of dose and of duration of treatment with clofazimine.

It is understood by the person of skill in the art that the present application also discloses each and any combination of the individual features disclosed herein.

Definitions

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, napthoic acid, oleic acid, palmitic acid, pamoic (emboic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobionic acid, tartaric acid, benzoic acid, cinnamic acid, mandelic acid, methanesulfonic acid, ethanesulfonic acid, p-toluenesulfonic acid, salicylic acid, and the like.

Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, histidine, arginine, lysine, benethamine, N-methyl-glucamine, and ethanolamine. Other acids include dodecylsufuric acid, naphthalene-1,5-disulfonic acid, naphthalene-2-sulfonic acid, and saccharin.

In accordance with the present invention, apart from the free base, the use of the methanesulfonic acid, maleic acid, isonicotinic acid, nicotinic acid, malonic acid, and salicylic acid salts, and in particular of clofazimine mesylate is preferred.

By the term "pharmaceutically acceptable derivative" as used herein, for example, compounds disclosed in U.S. Pat. No. 9,540,336 are meant, the disclosure of U.S. Pat. No. 9,540,336 is incorporated herein in its entirety. In addition, derivatives are meant as described in Lu, Y., Zhen, M., Wang, B., Fu, L., Zhao, W., Li, P., Xu, J., Zhu, H., Jin, H., Yin, D., Huang, H., Upton, A M. and Ma, Z., "Clofazimine Analogs with Efficacy against experimental Tuberculosis and reduced Potential for Accumulation" *Antimicrobial Agents and Chemotherapy* (2011), 55 (11): pp. 5185-5193. Additionally, The term, "pharmaceutically acceptable derivative" of a compound is, for example, a prodrug of said compound. In general, a prodrug is a derivative of a compound which, upon administration, is capable of providing the active form of the compound. Such derivatives, for example, may be an ester or amide of a carboxyl group, a carboxyl ester of a hydroxyl group, or a phosphate ester of a hydroxyl group.

By "therapeutically effective amount", "therapeutically effective dose", or "pharmaceutically effective amount" is meant an amount of clofazimine, or a pharmaceutically acceptable salt or derivative thereof, as disclosed for this invention, which has a therapeutic effect. The doses of clofazimine which are useful in treatment are therapeutically effective amounts. Thus, as used herein, a therapeutically effective amount means those amounts of clofazimine which produce the desired therapeutic effect as judged by clinical trial results and/or model animal infection studies.

The amount of the clofazimine and daily dose can be routinely determined by one of skill in the art, and will vary, depending on several factors, such as the particular microbial strain involved. This amount can further depend upon the patient's height, weight, sex, age and medical history. For prophylactic treatments, a therapeutically effective amount is that amount which would be effective to prevent a microbial infection.

A "therapeutic effect" relieves, to some extent, one or more of the symptoms of the infection, and includes curing an infection. "Curing" means that the symptoms of active infection are eliminated, including the total or substantial elimination of excessive members of viable microbe of those involved in the infection to a point at or below the threshold of detection by traditional measurements. However, certain long-term or permanent effects of the infection may exist even after a cure is obtained (such as extensive tissue damage). As used herein, a "therapeutic effect" is defined as a statistically significant reduction in bacterial load in a host, emergence of resistance, or improvement in infection symptoms as measured by human clinical results or animal studies.

"Treat", "treatment", or "treating" as used herein refers to administering a pharmaceutical composition/combination for prophylactic and/or therapeutic purposes.

The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of clofazimine.

Unless stated otherwise herein, the term "inhalation" is meant to refer to pulmonary inhalation.

Unless stated otherwise herein, the term "infection" as used herein is meant to refer to pulmonary infections.

Unless otherwise stated, the term "substantially" when used to refer to the purity of a compound, indicates a purity of compound of 95% or greater purity.

Unless otherwise stated, the term "appropriate particle size" refers to a particle size of clofazimine in a composition, or a composition that provides the desired therapeutic effect when administered to a patient.

Unless otherwise stated, the term "appropriate concentration" refers to a concentration of a component in a composition or combination which provides a pharmaceutically acceptable composition or combination.

Pharmaceutical Compositions and Combinations

The following water grades are particularly applicable to the present invention: sterile purified water, sterile water for injection, sterile water for irrigation, sterile water for inhalation (USP) and corresponding water grades in accordance with e.g. European Pharmacopoeia or National Formulary.

Aqueous electrolyte solutions as used in accordance with the present invention as the aqueous liquid carrier may further comprise sodium chloride, potassium chloride, lithium chloride, magnesium chloride, calcium chloride or mixtures thereof.

The aqueous liquid carrier is preferably isotonic saline solution (0.9% NaCl corresponding to about/approximately 150 mM NaCl, preferably 154 mM NaCl).

Clofazimine has been shown to exist in at least four polymorphic forms (see, for example, Bannigan, et al., "Investigation into the Solid and Solution Properties of Known and Novel Polymorphs of the Antimicrobial Molecule Clofazimine", Cryst. Growth Des. 2016, 16 (12), pp. 7240-7250). Clofazimine can exist in a triclinic form FI, a monoclinic form FII, and an orthorhombic form FIII. A further form FIV has also been seen only at high temperatures.

Accordingly, in a further embodiment of the invention a pharmaceutical composition is provided comprising:
(a) a therapeutically effective dose of clofazimine;
(b) a nonionic surfactant with an Hydrophilic-Lipophilic Balance value of greater than 10; and
(c) an aqueous liquid carrier selected from water, isotonic saline, buffered saline and aqueous electrolyte solutions wherein the clofazimine is provided in the form of particles in a suspension,
and wherein the particles of clofazimine have a median size of less than 5 μm and a D90 of less than 6 μm, preferably a median size of less than 2 μm and a D90 of less than 3 μm, and wherein the clofazimine is provided in a polymorphic form or forms selected from triclinic form FI, monoclinic form FII and orthorhombic form FIII and mixtures of such forms. In another embodiment, the clofazimine is provided substantially in orthorhombic form FIII.

In a further embodiment of the invention a pharmaceutical composition according to any of the composition embodiments herein described is provided wherein the nonionic surfactant is selected from polysorbate 20 (for example Tween® 20, polysorbate 60 (for example Tween® 60), polysorbate 80 (for example Tween® 80), stearyl alcohol, a polyethylene glycol derivative of hydrogenated castor oil with an Hydrophilic-Lipophilic Balance value of 14 to 16 (for example Cremophor® RH 40), a polyethylene glycol derivative of hydrogenated castor oil with an Hydrophilic-Lipophilic Balance value of 15 to 17 (for example Cremophor® RH 60), sorbitan monolaurate (for example Span® 20), sorbitan monopalmitate (for example Span® 40), sorbitan monostearate (for example Span® 60), polyoxyethylene (20) oleyl ether (for example Brij® O20), polyoxyethylene (20) cetyl ether (for example Brij® 58), polyoxyethylene (10) cetyl ether (for example Brij® O10), polyoxyethylene (10) oleyl ether (for example Brij® O10), polyoxyethylene (100) stearyl ether (for example Brij® S100), polyoxyethylene (10) stearyl ether (for example Brij® S10), polyoxyethylene (20) stearyl ether (for example Brij® S20), polyoxyethylene (4) lauryl ether (for example Brij® L4), polyoxyethylene (20) cetyl ether (for example Brij® 93), polyoxyethylene (2) cetyl ether (for example Brij® S2), caprylocaproyl polyoxyl-8 glyceride (for example Labrasol®), polyethylene glycol (20) stearate (for example Myrj™ 49), polyethylene glycol (40) stearate (for example Myrj™ S40), polyethylene glycol (100) stearate (for example Myrj™ S100), polyethylene glycol (8) stearate (for example Myrj™ S8), and polyoxyl 40 stearate (for example Myrj™ 52), and mixtures thereof.

In another embodiment of the invention, a pharmaceutical composition according to any of the composition embodiments described herein is provided, wherein the non-ionic surfactant is polysorbate 80, and wherein the aqueous liquid carrier is distilled water, hypertonic saline or isotonic saline. In another embodiment of the invention, a pharmaceutical composition is provided wherein the hypertonic saline is from 1% to 7% (w/v) sodium chloride. In a further embodiment of the invention, a pharmaceutical composition is provided wherein the non-ionic surfactant is ultrapure polysorbate 80 (for example NOF Corporation Polysorbate 80 (Hx2)), and wherein the aqueous liquid carrier is isotonic saline.

In another embodiment of the invention, a pharmaceutical composition according to any one of the composition embodiments described herein is provided wherein the osmolality of the composition is in the range of 200-700 mOsm/kg. In a further embodiment, the osmolality of the composition is in the range of 300-400 mOsm/kg.

In a further embodiment of the invention, a pharmaceutical composition according to any one of the composition embodiments described herein, is provided wherein the nonionic surfactant is in the range of 0.001% to 5% (v/v) of the total composition and the amount of clofazimine is in the range of 0.1% to 20% (w/v) of the total composition.

In another embodiment of the invention, a pharmaceutical composition according to any one of the composition embodiments described herein is provided, wherein the pharmaceutical composition is prepared by a process comprising the following steps:
(1) homogenization of a suspension of clofazimine, the nonionic surfactant and water to obtain a suspension comprising clofazimine of an appropriate particle size,
(2) adjusting the pH of the suspension resulting from (1) to a pH of between pH 5.5 and pH 7.5, and
(3) adjusting the sodium chloride concentration to an appropriate concentration and
(4) adjusting the osmolality to an appropriate level.

In a further embodiment, the pH is adjusted to 7.4, and the sodium chloride concentration is adjusted to 154 mM sodium chloride. In another embodiment, the homogenization in step (1) is carried out by high pressure homogenization, high shear homogenization, wet milling, ultrasonic homogenization, or a combination of such processes. In another aspect, the homogenization of clofazimine is carried out in multiple steps of homogenization. In another embodiment, the appropriate particle size of the clofazimine are particles having a mean size of less than 5 μm and D90 of less than 6 μm. In a further embodiment, the appropriate particle size of clofazimine are particles having a mean size of less than 2 μm and D90 of less than 3 μm.

In a further embodiment of the invention, a pharmaceutical composition according to any one of the composition embodiments described herein is provided, wherein the pharmaceutical composition is prepared by a process comprising the following steps:
(1) homogenization of a suspension of clofazimine and a non-aqueous liquid to obtain a suspension comprising clofazimine of an appropriate particle size, (2) isolation of the clofazimine,
(3) addition of the clofazimine to the nonionic surfactant and water,
(4) adjusting the pH of the suspension resulting from (3) to a pH of between pH 5.5 and pH 7.5, and
(5) adjusting the sodium chloride concentration to an appropriate concentration.

In a further embodiment, the pH is adjusted to 7.4, and the sodium chloride concentration is adjusted to 154 mM sodium chloride. In a further embodiment, the homogenization in step (1) is carried out by high pressure homogenization, high shear homogenization, wet milling, ultrasonic homogenization, or a combination of such processes. In another embodiment, the homogenization of clofazimine is carried out in multiple steps of homogenization. In another embodiment, the appropriate particle size of the clofazimine are particles having a mean size of less than 5 µm and D90 of less than 6 µm. In a further embodiment, the appropriate particle size of clofazimine are particles having a mean size of less than 2 µm and D90 of less than 3 µm.

In a further embodiment, a pharmaceutical composition according to any one of the composition embodiments described herein is provided, wherein the composition is prepared by a process comprising the following steps:
(1) micronization of clofazimine to obtain clofazimine of an appropriate particle size,
(2) addition of the clofazimine to the nonionic surfactant and water,
(3) adjusting the pH of the suspension resulting from (2) to a pH of between pH 5.5 and pH 7.5, and
(4) adjusting the sodium chloride concentration to an appropriate concentration.

In a further embodiment, the pH is adjusted to 7.4, and the sodium chloride concentration is adjusted to 154 mM sodium chloride.

In another embodiment, the micronization of the clofazimine is carried out by jet milling, spray drying, ball milling, or super critical fluids processing. In another embodiment, the micronization of clofazimine is carried out in multiple steps of micronization. In another embodiment, the appropriate particle size of the clofazimine are particles having a mean size of less than 5 µm and D90 of less than 6 µm. In a further embodiment, the appropriate particle size of clofazimine are particles having a mean size of less than 2 µm and D90 of less than 3 µm.

In a further embodiment, a pharmaceutical composition according to any one of the composition embodiments described herein is provided, wherein the composition is prepared by a process comprising homogenization of a suspension of clofazimine in the nonionic surfactant, water containing an appropriate concentration of sodium chloride, and which has been adjusted to a pH of between pH 5.5 and pH 7.5, to obtain clofazimine of an appropriate particle size. In a further embodiment, the pH is adjusted to 7.4, and the sodium chloride concentration is adjusted to 154 mM sodium chloride. In a further embodiment, the homogenization is carried out by high pressure homogenization, high shear homogenization, wet milling, ultrasonic homogenization, or a combination of such processes. In another embodiment, the homogenization of clofazimine is carried out in multiple steps of homogenization. In another embodiment, the appropriate particle size of the clofazimine are particles having a mean size of less than 5 µm and D90 of less than 6 µm. In a further embodiment, the appropriate particle size of clofazimine are particles having a mean size of less than 2 µm and D90 of less than 3 µm.

In another embodiment, a process for the preparation of a pharmaceutical composition according to any of the composition embodiments described herein is provided, comprising the following steps:
(1) homogenization of a suspension of clofazimine, the non-ionic surfactant and water to obtain a suspension comprising clofazimine of an appropriate particle size,
(2) adjusting the pH of the suspension resulting from (1) to a pH of between pH 5.5 and pH 7.5, and
(3) adjusting the sodium chloride concentration to an appropriate concentration, and
(4) adjusting the osmality to an appropriate level.

In another embodiment, the pH is adjusted to 7.4, and the sodium chloride concentration is adjusted to 154 mM sodium chloride. In a further embodiment, the homogenization is carried out by high pressure homogenization, wet milling, ultrasonic homogenization, or a combination of such processes. In a further embodiment, the homogenization of clofazimine is carried out in multiple steps of homogenization. In a further embodiment, the appropriate particle size of clofazimine are particles having a mean size of less than 5 µm and a D90 of less than 6 µm. In another embodiment, the appropriate particle size of clofazimine are particles having a mean size of 2 µm and a D90 of less than 3 µm.

In another embodiment, a process for the preparation of any of the pharmaceutical composition embodiments as described herein is provided, wherein
(1) homogenization of a suspension of clofazimine and a non-aqueous liquid to obtain a suspension comprising clofazimine of the appropriate particle size,
(2) isolation of the clofazimine,
(3) addition of the clofazimine to the nonionic surfactant and water,
(4) adjusting the pH of the suspension resulting from (3) to a pH of between pH 5.5 and pH 7.5, and
(5) adjusting the sodium chloride concentration to an appropriate concentration.

In another embodiment, the pH is adjusted to 7.4, and the sodium chloride concentration is adjusted to 154 mM sodium chloride. In a further embodiment, the homogenization is carried out by high pressure homogenization, wet milling, ultrasonic homogenization, or a combination of such processes. In a further embodiment, the homogenization of clofazimine is carried out in multiple steps of homogenization. In a further embodiment, the appropriate particle size of clofazimine are particles having a mean size of less than 5 µm and a D90 of less than 6 µm. In another embodiment, the appropriate particle size of clofazimine are particles having a mean size of 2 µm and a D90 of less than 3 µm.

In a further embodiment, a process for the preparation of a pharmaceutical composition according to any one of the pharmaceutical composition embodiments as described herein is provided, comprising the following steps:
(1) micronization of clofazimine to obtain clofazimine of an appropriate particle size,
(2) addition of the clofazimine to the nonionic surfactant and water,
(3) adjusting the pH of the suspension resulting from (2) to a pH of between pH 5.5 and pH 7.5, and
(4) adjusting the sodium chloride concentration to an appropriate concentration.

In another embodiment, the pH is adjusted to 7.4, and the sodium chloride concentration is adjusted to 154 mM sodium chloride. In a further embodiment, the micronization of the clofazimine is carried out by jet milling, spray drying, ball milling, or super critical fluids processing. In a further embodiment, the micronization of clofazimine is carried out in multiple steps of micronization. In a further embodiment, the appropriate particle size of clofazimine are particles having a mean size of less than 5 μm and a D90 of less than 6 μm. In another embodiment, the appropriate particle size of clofazimine are particles having a mean size of 2 μm and a D90 of less than 3 μm.

In another embodiment, a process for the preparation of a pharmaceutical composition according to any one of pharmaceutical composition embodiment described herein is provided, comprising homogenization of a suspension of clofazimine in the nonionic surfactant, water containing an appropriate concentration of sodium chloride, and which has been adjusted to a pH of between pH 5.5 and pH 7.5, to obtain clofazimine of an appropriate particle size. In another embodiment, the pH is 7.4, and the appropriate concentration of sodium chloride is 154 mM sodium chloride. In a further embodiment, the homogenization is carried out by high pressure homogenization, wet milling, ultrasonic homogenization, or a combination of such processes. In a further embodiment, the homogenization of clofazimine is carried out in multiple steps of homogenization. In a further embodiment, the appropriate particle size of clofazimine are particles having a mean size of less than 5 μm and a D90 of less than 6 μm. In another embodiment, the appropriate particle size of clofazimine are particles having a mean size of 2 μm and a D90 of less than 3 μm.

In a further embodiment a process for the preparation of a pharmaceutical composition according to any one of composition embodiments described herein, is provided, comprising the following steps: (a) homogenization of a suspension of clofazimine, the non-ionic surfactant and water to obtain a suspension comprising clofazimine of an appropriate particle size; (b) adjusting the pH of the resulting suspension a pH of between pH 5.5 and pH 7.5; (c) adjusting the sodium chloride concentration to an appropriate concentration, and (d) adjusting the osmality to an appropriate level; and wherein steps (b), (c) and (d), may occur in the order of (b), (c), (d); (b), (d), (c); (c), (b), (d); (c), (d), (b); (d), (b), (c); or (d), (c), (b).

In another embodiment, a process for the preparation of a pharmaceutical composition according to any one of the composition embodiments described herein, is provided comprising the following steps: (a) homogenization of a suspension of clofazimine and a non-aqueous liquid to obtain a suspension comprising clofazimine of the appropriate particle size; (b) isolation of the clofazimine; (c) addition of the clofazimine to the nonionic surfactant and water; (d) adjusting the pH of to resulting suspension to a pH of between pH 5.5 and pH 7.5; and (e) adjusting the sodium chloride concentration to an appropriate concentration; and wherein steps (d) and (e) may occur in the order of (d), (e); or (e), (d).

In another embodiment, a process for the preparation of a pharmaceutical composition according to any one or the composition embodiments described herein, is provided, comprising the following steps: (a) micronization of clofazimine to obtain clofazimine of an appropriate particle size, and (b) addition of the clofazimine to the nonionic surfactant, water containing an appropriate concentration of sodium chloride, and which has been adjusted to a pH of between between pH 5.5 and 7.5.

In another embodiment of the present invention, a pharmaceutical combination in the form of an aerosol for inhalation is provided, prepared by aerosolization of the composition according to any one of the composition embodiments described herein, by a nebulizing device selected from an ultrasonic nebulizer, an electron spray nebulizer, a vibrating membrane nebulizer, a jet nebulizer and a mechanical soft mist inhaler, and wherein the aerosol particles produced by the nebulizing device have a mass median aerodynamic diameter of 1 to 5 μm. In a further embodiment, the aerosol for inhalation is for lower lung deposition. In another embodiment, the nebulizing device exhibits an output rate of 0.1 to 1.0 ml/min. In another embodiment, the total inhalation volume is between 1 ml and 5 ml.

In another embodiment, a pharmaceutical composition according to any one of the composition embodiments described herein is provided which is for use in combination with an agent for dispersing and/or destruction of biofilm, with mucolytic and/or mucoactive agents, and/or agents that reduce biofilm formation selected from nebulized 4-7% hypertonic saline, metaperiodate, sodium dodecyl sulfate, sodium bicarbonate, tromethamine, silver nano particles, bismuth thiols, ethylene diamine tetraacetic acid, gentamicin loaded phosphatidylcholine-decorated gold nanoparticles, chelators, cis-2-decenoic acid, D-amino acids, D-enantiomeric peptides, gallium mesoporphyrin IX, gallium protoporphyrin IX, curcumin, patulin, penicillic acid, baicalein, naringenin, ursolic acid, asiatic acid, corosolic acid, fatty acids, host defense peptides, and antimicrobial peptides. In another embodiment, the composition for the use is administered before, simultaneously, or subsequently to the administration of an agent selected from bedaquiline or a pharmaceutically acceptable salt or derivative thereof, cefoxitine, amikacin, clarithromycin, pyrazinamide, rifampin, moxifloxacin, levofloxacin, and para-amino salicylate, and mixtures thereof.

In another embodiment, a pharmaceutical combination according to any of the combination embodiments described herein is provided which is for use in combination with an agent for dispersing and/or destruction of biofilm, with mucolytic and/or mucoactive agents, and/or agents that reduce biofilm formation selected from nebulized 4-7% hypertonic saline, metaperiodate, sodium dodecyl sulfate, sodium bicarbonate, tromethamine, silver nano particles, bismuth thiols, ethylene diamine tetraacetic acid, gentamicin loaded phosphatidylcholine-decorated gold nanoparticles, chelators, cis-2-decenoic acid, D-amino acids, D-enantiomeric peptides, gallium mesoporphyrin IX, gallium protoporphyrin IX, curcumin, patulin, penicillic acid, baicalein, naringenin, ursolic acid, asiatic acid, corosolic acid, fatty acids, host defense peptides, and antimicrobial peptides. In another embodiment, the combination for the use is used to administer a composition of the present invention before, simultaneously, or subsequently to the administration of an agent selected from bedaquiline or a pharmaceutically acceptable salt or derivative thereof, cefoxitine, amikacin, clarithromycin, pyrazinamide, rifampin, moxifloxacin, levofloxacin, and para-amino salicylate, and mixtures thereof. In another embodiment, the composition is administered before, simultaneously or subsequently to the administration of an agent selected from bedaquiline or a pharmaceutically acceptable salt or derivative thereof, and amikacin, and mixtures thereof. In a further embodiment, the composition is administered before, simultaneously or subsequently to the administration of bedaquiline or a pharmaceutically acceptable salt or derivative thereof.

In another embodiment, a pharmaceutical composition according to any one of the composition embodiments as described herein is provided for use in the treatment and/or prophylaxis of a pulmonary infection caused by mycobacteria or other gram positive bacteria. In a further embodiment, the infection is caused by a species of the genus mycobacterium selected from nontuberculous mycobacteria and Mycobacterium tuberculosis complex, and a combination thereof. In a further embodiment, the nontuberculous mycobacteria is selected from *Mycobacterium avium, Mycobacterium intracellulare, Mycobacterium abscessus*, and *Mycobacterium leprae*, and a combination thereof. In another embodiment, the infection is an opportunistic infection, selected from MAC pulmonary disease and nontuberculous infection, in a patient with cystic fibrosis, chronic obstructive pulmonary or acquired immune deficiency syndrome. In another embodiment, the infection is an opportunistic nontuberculous mycobacteria infection in patients with cystic fibrosis. In another embodiment, the composition for the use is administered before, simultaneously, or subsequently to the administration of an agent selected from bedaquiline or a pharmaceutically acceptable salt or derivative thereof, cefoxitine, amikacin, clarithromycin, pyrazinamide, rifampin, moxifloxacin, levofloxacin, and para-amino salicylate, and mixtures thereof. In another embodiment, the composition is administered before, simultaneously or subsequently to the administration of an agent selected from bedaquiline or a pharmaceutically acceptable salt or derivative thereof, and amikacin, and mixtures thereof. In a further embodiment, the composition is administered before, simultaneously or subsequently to the administration of bedaquiline or a pharmaceutically acceptable salt or derivative thereof.

In another embodiment a pharmaceutical combination according to any of the combination embodiments as described herein is provided for use in the treatment and/or prophylaxis of a pulmonary infection caused by mycobacteria or other gram positive bacteria. In a further embodiment, the infection is caused by a species of the genus mycobacterium selected from nontuberculous mycobacteria and *Mycobacterium tuberculosis* complex, and a combination thereof. In a further embodiment, the nontuberculous mycobacteria is selected from *Mycobacterium avium, Mycobacterium intracellulare, Mycobacterium abscessus*, and *Mycobacterium leprae*, and a combination thereof. In another embodiment, the infection is an opportunistic infection, selected from MAC pulmonary disease and nontuberculous infection, in a patient with cystic fibrosis, chronic obstructive pulmonary or acquired immune deficiency syndrome. In another embodiment, the infection is an opportunistic nontuberculous mycobacteria infection in patients with cystic fibrosis. In another embodiment, the combination for the use is used to administer a composition of the present invention before, simultaneously, or subsequently to the administration of an agent selected from bedaquiline or a pharmaceutically acceptable salt or derivative thereof, cefoxitine, amikacin, clarithromycin, pyrazinamide, rifampin, moxifloxacin, levofloxacin, and para-amino salicylate, and mixtures thereof. In another embodiment, the combination for the use is used to administer a composition of the present invention before, simultaneously or subsequently to the administration of an agent selected from bedaquiline or a pharmaceutically acceptable salt or derivative thereof, and amikacin, and mixtures thereof. In another embodiment, the combination for the use is used to administer a composition of the present invention before, simultaneously or subsequently to the administration of bedaquiline or a pharmaceutically acceptable salt or derivative thereof.

In another embodiment, a system for use in providing antibiotic activity when treating or providing prophylaxis against a pulmonary infection caused by mycobacteria or other gram-positive bacteria is provided wherein the system comprises:
1) a nebulized pharmaceutical combination comprising:
   (a) a therapeutically effective dose of clofazimine;
   (b) a nonionic surfactant with an Hydrophilic-Lipophilic Balance value of greater than 10; and
   (c) an aqueous liquid carrier selected from water, isotonic saline, buffered saline and aqueous electrolyte solutions and
2) a nebulizer,
wherein the clofazimine is present in the form of a suspension,
and
wherein the aerosol particles produced by the system have a mass median aerodynamic diameter of 1 to 5 µm.

In a further embodiment, a pharmaceutical composition according to any one of composition embodiments described herein is provided, for use in the treatment and/or prophylaxis of pulmonary fungal infections or *Clostridium difficile*, or a combination thereof. In another embodiment, a pharmaceutical composition according to any one of composition embodiments described herein is provided, for use in the treatment and/or prophylaxis of pulmonary fungal infections. In a further embodiment, the pulmonary fungal infection is *Candida albicans* or *Aspergillus fumigatus*, or a combination thereof.

In a further embodiment, a pharmaceutical combination according to any one of the combination embodiments described herein is provided, for use in the treatment and/or prophylaxis of pulmonary fungal infections or *Clostridium difficile*, or a combination thereof. a pharmaceutical combinations according to any one of combinations embodiments described herein is provided, for use in the treatment and/or prophylaxis of pulmonary fungal infections. In a further embodiment, the pulmonary fungal infection is *Candida albicans* or *Aspergillus fumigatus*, or a combination thereof.

In another embodiment, a method of treatment or prophylaxis of a pulmonary infection is provided, in a patient in need thereof, comprising administering by inhalation a composition according to any one the composition embodiments described herein. In another embodiment, the infection is caused by a species of the genus mycobacterium selected from nontuberculous mycobacteria and Mycobacterium tuberculosis complex, and a combination thereof. In a further embodiment, the nontuberculous mycobacterium is selected from *Mycobacterium avium, Mycobacterium intracellulare, Mycobacterium abscessus*, and *Mycobacterium leprae*, and a combination thereof. In a further embodiment, the infection is an opportunistic infection, selected from MAC pulmonary disease and nontuberculous infection, in a patient with cystic fibrosis, chronic obstructive pulmonary disease or acquired immune deficiency syndrome. In another embodiment, the infection is an opportunistic nontuberculous mycobacteria infection in a patient with cystic fibrosis.

In a further embodiment, a method of treatment or prophylaxis of a pulmonary infection is provided caused by mycobacteria or other gram positive bacteria, in a patient in need thereof, comprising administering by inhalation a composition according to any one of the composition embodiments described herein, before, simultaneously, or subsequently to the administration of an agent selected from bedaquiline, or a pharmaceutically acceptable salt of derivative thereof, cefoxitine, amikacin, clarithromycin, pyrazinamide, rifampin, moxifloxacin, levofloxacin, and para-amino salicylate, and mixtures thereof. In another embodiment, the agent is bedaquiline or amikacin. In a further embodiment, the agent is bedaquiline.

Particle Size and Distribution

The therapeutic effect of aerosolized therapies is dependent upon the dose deposited and its distribution. Aerosol particle size is one of the important variables in defining the dose deposited and the distribution of drug aerosol in the lung.

Generally, inhaled aerosol particles are subject to deposition by one of two mechanisms: impaction, which usually predominates for larger aerosol particles, and sedimentation, which is prevalent for smaller aerosol particles. Impaction occurs when the momentum of an inhaled aerosol particle is large enough that the particle does not follow the air stream and encounters a physiological surface. In contrast, sedimentation occurs primarily in the lower lung when very small aerosol particles which have traveled with the inhaled air stream encounter physiological surfaces as a result of gravitational settling.

Pulmonary drug delivery may be accomplished by inhalation of an aerosol through the mouth and throat. Aerosol particles having an aerodynamic diameter of greater than about 5 µm generally do not reach the lung; instead, they tend to impact the back of the throat and are swallowed and possibly orally absorbed. Aerosol particles having diameters of about 3 to about 5 µm are small enough to reach the upper- to mid-pulmonary region (conducting airways), but are too large to reach the alveoli. Smaller aerosol particles, i.e. about 0.5 to about 3 µm, are capable of reaching the alveolar region. Aerosol particles having diameters smaller than about 0.5 µm tend to be exhaled during tidal breathing, but can also be deposited in the alveolar region by a breath hold.

Aerosols used in pulmonary drug delivery are made up of a wide range of aerosol particle sizes, so statistical descriptors are used. Aerosols used in pulmonary drug delivery are typically described by their mass median diameter (MMD), that is, half of the mass is contained in aerosol particles larger than the MMD, and half the mass is contained in aerosol particles smaller than the MMD. For particles with uniform density, the volume median diameter (VMD) can be used interchangeably with the MMD. Determinations of the VMD and MMD are made by laser diffraction. The width of the distribution is described by the geometric standard deviation (GSD). However, the deposition of an aerosol particle in the respiratory tract is more accurately described by the particle's aerodynamic diameter, thus, the mass median aerodynamic diameter is typically used. MMAD determinations are made by inertial impaction or time of flight measurements. For aqueous particles, VMD, MMD and MMAD should be the same. However, if humidity is not controlled as the aerosol transits the impactor, MMAD determinations will be smaller than MMD and VMD due to dehydration. For the purposes of this description, VMD, MMD and MMAD measurements are considered to be under controlled conditions such that descriptions of VMD, MMD and MMAD will be comparable.

Nonetheless, for the purpose of the description, the aerosol particle size of the aerosol particles will be given as MMAD as determined by measurement at room temperature with a Next Generation Impactor (NGI) in accordance with US Pharmacopeial Convention. In Process Revision <601> Aerosols, Nasal Sprays, Metered-Dose Inhalers, and Dry Powder Inhalers, Pharmacopeial Forum (2003), Volume Number 29, pages 1176-1210 also disclosed in Jolyon Mitchell, Mark Nagel "Particle Size Analysis of Aerosols from Medicinal Inhalers", KONA Powder and Particle Journal (2004), Volume 22, pages 32-65.

In accordance with the present invention, the particle size of the aerosol is optimized to maximize the deposition of clofazimine at the site of infection and to maximize tolerability. Aerosol particle size may be expressed in terms of the mass median aerodynamic diameter (MMAD). Large particles (e.g., MMAD>5 µm) tend to deposit in the extrathoracic and upper airways because they are too large to navigate bends in the airways. Intolerability (e.g., cough and bronchospasm) may occur from upper airway deposition of large particles.

Thus, in accordance with a preferred embodiment, the MMAD of the aerosol should be less than about 5 µm, preferably between about 1 and 5 µm, more preferably below 3 µm (<3 µm).

However, a guided breathing maneuver can be used to allow larger particles to pass through the extrathoracic and upper airways and deeper into the lungs than during tidal breathing which will increase the central and lower lung deposition of the aerosol. A guided breathing maneuver may be as slow as 100 ml/min. Thus, when used with a guided breathing maneuver, the preferred MMAD of the aerosol should be less than about 10 µm.

Another equally important factor (in addition to aerosol particle size) is the particle size and size distribution of the solid particles, in this case clofazimine particle size and distribution. The size of a solid particle in a given aerosol particle must be smaller than the aerosol particle in which it is contained. A larger aerosol particle may contain one or more solid particles. Further, when dealing with dilute suspensions, a majority of aerosol particles may contain no solid particle.

Because of this, it is desirable to have solid drug particles that are significantly smaller than the MMAD of the aerosol particles. For example, if MMAD of the aerosol particles is 3 µm, than a desired solid particle would be 1 µm, or smaller.

Another consideration, for example when using a vibrating mesh nebulizer, the formulation is pumped through orifices in a plate, which breaks up the suspension into droplets. It follows, then, that the solid particles must also be smaller than these orifices, in order to pass through.

Solid particle size in the suspension may be given by the mean size of the particles, and also by the distribution of the particles. D90 values indicate that 90% of the particles within the suspension are of the mean size or smaller.

Nebulizer

For aqueous and other non-pressurized liquid systems, a variety of nebulizers (including small volume nebulizers) are available to aerosolize the formulations. Compressor-driven nebulizers incorporate jet technology and use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers rely on mechanical energy in the form of vibration of a piezoelectric crystal to generate respirable liquid droplets and are commercially available from, for example, Omron Heathcare, Inc. and DeVilbiss Health Care, Inc. Vibrating mesh nebulizers rely upon either piezoelectric or mechanical pulses to respirable liquid droplets generate. Other examples of nebulizers for use with clofazimine described herein are described in U.S. Pat. Nos. 4,268,460; 4,253,468; 4,046,146; 3,826,255; 4,649,911; 4,510,929; 4,624,251; 5,164,740; 5,586,550; 5,758,637; 6,644,304; 6,338,443; 5,906,202; 5,934,272;

5,960,792; 5,971,951; 6,070,575; 6,192,876; 6,230,706; 6,349,719; 6,367,470; 6,543,442; 6,584,971; 6,601,581; 4,263,907; 5,709,202; 5,823,179; 6,192,876; 6,644,304; 5,549,102; 6,083,922; 6,161,536; 6,264,922; 6,557,549; and 6,612,303, all of which are hereby incorporated by reference in their entirety. Commercial examples of nebulizers that can be used with the clofazimine compositions described herein include Respirgard II®, Aeroneb®, Aeroneb® Pro, and Aeroneb® Go produced by Aerogen; AERx® and AERx Essence™ produced by Aradigm; Porta-Neb®, Freeway Freedom™, Sidestream, Ventstream and I-neb produced by Respironics, Inc.; and PARI LCPlus®, PARI LC-Star®, and e-Flow7m produced by PARI, GmbH. Further non-limiting examples are disclosed in U.S. Pat. No. 6,196,219.

In accordance with the present invention, the pharmaceutical composition may be preferably aerosolized using a nebulising device selected from an ultrasonic nebulizer, an electron spray nebulizer, a vibrating membrane nebulizer, a jet nebulizer or a mechanical soft mist inhaler.

It is preferred that the device controls the patient's inhalation flow rate either by an electrical or mechanical process.

In a further preferred embodiment, the aerosol production by the device is triggered by the patient's inhalation, such as with an AKITA device.

Preferred (commercially available) examples of the above nebulizers/devices to be used in accordance with the present invention are Vectura fox, Pari eFlow, Pari Trek S, Philips Innospire mini, Philips InnoSpire Go, Medspray device, Aeroneb Go, Aerogen Ultra, Respironics Aeroneb, Akita, Medspray Ecomyst and Respimat.

Use in Treatment and/or Prophylaxis

The pharmaceutical compositions and pharmaceutical combinations (aerosols, aerosolized formulations) and systems according to the present invention are intended for the use in the treatment and/or prophylaxis of pulmonary infections caused by mycobacteria or other clofazimine susceptible bacteria, such as *Staphylococcus aureus* (including methicillin-resistant and vancomycin intermediate-resistant strains), *Streptococcus pneumoniae*, and *Enterococcus* spp. The pharmaceutical compositions and pharmaceutical combinations of the present invention may also be used for the treatment and/or prophylaxis of pulmonary fungal infections.

Dosing of Clofazimine

In accordance with the present invention, the pharmaceutical composition is delivered by nebulization in about 1-5 ml, preferably 1-2 ml of the pharmaceutical composition of the invention.

Thus, the target fill dose is about 1-5 ml corresponding to 20-100 mg clofazimine, based on a clofazimine concentration in the pharmaceutical composition of about 20 mg/ml.

The daily lung dose (i.e. the dose deposited in the lung) of clofazimine to be administered in accordance with the present invention is about 5-10 mg, which corresponds to a nominal dose of 15-30 mg (device dose) in the case of *M. abscessus* infections.

It is understood that the person of skill in the art will routinely adjust the lung dose of clofazimine to be administered (and thus the fill/nominal dose/the volume to be nebulized) based on the minimum inhibitory concentration (MIC) of clofazimine for the respective bacteria strain well established in the art.

Depending on the dosing frequency, once or twice per day, the daily lung dose will be split accordingly.

In accordance with the present invention, clofazimine is to be administered once or twice daily with a resulting total daily lung dose of about 5 to 10 mg.

It will be obvious to a person skilled in the art that the above amounts relate to clofazimine free base, the dosage amounts for derivatives, and salts will have to be adjusted accordingly based on the MIC of the respective compound and strain.

Mucolytic Agents/Biofilm Modifying Agents

In order to reduce sputum viscosity during aerosol treatment and to destroy existing biofilm, the treatment and/or prophylaxis according with the present invention can involve additional administration of mucolytic and/or biofilm destructing agents.

These agents can be prepared in fixed combination or be administered simultaneously or subsequently to the pharmaceutical composition/aerosol combination comprising clofazimine in accordance with the present invention.

Agents for dispersing/destruction of the biofilm, mucolytic and/or mucoactive agents and/or agents that reduce biofilm formation to be used in accordance with the present invention are selected from nebulized 4-7% hypertonic saline, metaperiodate, sodium dodecyl sulfate, sodium bicarbonate, tromethamine, silver nano particles, bismuth thiols, ethylene diamine tetraacetic acid, gentamicin loaded phosphatidylcholine-decorated gold nanoparticles, chelators, cis-2-decenoic acid, D-amino acids, D-enantiomeric peptides, gallium mesoporphyrin IX, gallium protoporphyrin IX, curcumin, patulin, penicillic acid, baicalein, naringenin, ursolic acid, asiatic acid, corosolic acid, fatty acids, host defense peptides, and antimicrobial peptides.

Furthermore, also other pharmaceutically active agents may be used in combination with the pharmaceutical compositions/aerosol combinations in accordance with the present invention. Such active agents may be selected from bedaquiline or a pharmaceutically acceptable salt or derivative thereof, cefoxitine, amikacin, clarithromycin, pyrazinamide, rifampin, moxifloxacin, levofloxacin, and para-amino salicylate, and mixtures thereof.

These agents can be prepared in fixed combination or be administered prior to, simultaneously or subsequently to the pharmaceutical composition/aerosol combination comprising clofazimine in accordance with the present invention.

EXAMPLES

The following examples serve to more fully describe the manner of using the above-described invention, as well as to set forth the best modes contemplated for carrying out various aspects of the invention. The Examples according to the invention are those falling within the scope of the claims herein.

Experimental

The exemplary compositions and combinations below have been prepared in accordance with the processes described herein.

Example 1

200 mg of clofazimine (as triclinic form I), 90 mg of sodium chloride, and 9.5 ml of water were mixed in an Ultra-Turrax homogenizer two times at 10,000 rpm for 5 minutes. 0.5 ml of polysorbate 80 (NOF Hx2) was added. This mixture was treated with an ultrasonic probe (Branson Digital Sonifier™ 250D with Bandelin Sonoplus Probe MS73) seven times, 3 minutes each, with an amplitude of 70%. The volume was adjusted to 10 ml with water. This suspension was filtered through VWR folded qualitative filter paper (303, particle retention 5-13 µm, Size: 150 mm), to give the Composition of Example 1. The composition of Example 1 had a median particle size of clofazimine of 3.9 µm, with a D90 of 6.7 µm. The concentration of clofazimine was determined by ultraviolet/visible spectroscopy at 280 nm, calibrating with a stock solution of 1 mg/ml of clofazimine diluted in the mobile phase, and determined to be 7.16 mg/ml.

The composition of Example 1 is shown in Table 1

TABLE 1

| | |
|---|---|
| Clofazimine Form FI | 71.6 mg |
| Polysorbate 80 (NOF Hx2) | 0.5 ml |
| Sodium chloride | 90.0 mg |
| Water (V/V) | 9.5 ml |

Preparation of Clofazimine of Orthorhombic Form III

A slurry of clofazimine (10 g) in toluene (20 ml) was stirred at 40° C. in an oil bath for 72 hours using a magnetic stirrer at 800 rpm. The solid portion of the slurry was collected by filtration through a crucible and dried at a maximum temperature of 40° C. under vacuum in an oven. This yielded 8.64 g of clofazimine as substantially pure (≥98%) orthorhombic form III.

Example 2

A suspension containing 6 g of clofazimine of orthorhombic form III in 100 ml of water containing 0.5% polysorbate 80 (NOF Hx2) and 0.6% sodium chloride was pre-micronized for approximately 40 seconds at 10,000 rpm using an Ultra-Turrax®. The pre-formulation was prepared by adding 0.6% sodium chloride in water to give a volume of 300 ml. 300 ml of this suspension was added into the inlet of the homogenizer, a M-110EH-30 microfluidizer (Microfluidics, Westwood, MA, USA) and a pre-homogenization step was performed for 15 minutes by circulation of the suspension through the H30Z chamber at 5,000 psi. Subsequently, the second H10Z chamber was installed in series with the first chamber and the suspension was further homogenized for 23 minutes at 25,000 psi. Particle size analysis was performed with a HORIBA LA 950 indicating a median particle size of 0.83 µm with a D90 value of 1.17 µm. A concentration of clofazimine of 16.05 mg/ml was determined by ultraviolet/visible spectroscopy at 280 nm, calibrating with a stock solution of 1 mg/ml of clofazimine diluted in the mobile phase.

The composition of Example 2 is shown in Table 2

TABLE 2

| Composition of Example 2 | |
|---|---|
| Clofazimine form III | 4.81 g (16.05 mg/ml) |
| Polysorbate 80 (NOF Hx2) | 1.5 ml (0.5% v/v) |
| Sodium Chloride | 1.8 g (0.6% w/v) |
| Water | 298.5 ml |

Example 3

A suspension of clofazimine (crystal modification orthorhombic Form III) in a solution of water, sodium chloride and Polysorbate 80, was treated using a M-110EH-30 Microfluidizer® Processor (chambers: H30Z and G10Z) operated for 30 minutes at a pressure of 28,250 psi, with the H30Z-G10Z configuration to produce the Composition of Example 3, with the resulting particles of clofazimine having a median particle size of 1.28 µm and a D90 below 2 µm. The composition of Example 3 is shown in Table 3.

TABLE 3

| Composition of Example 3 | |
|---|---|
| Clofazimine (Form FIII) | 20 mg/ml |
| Polysorbate 80 (NOF Hx2) | 0.5% (v/v) |
| Sodium Chloride | 0.9% (w/v) |
| Water | 99.5% (v/v) |

Viscosity Measurements

The viscosity of the Composition of Example 3 was tested using a STRESSTECH Rheometer in stress control mode. A double gap geometry was utilized and the spindle was continuously rotated to ensure the particulates remained in suspension during temperature points. Viscosity was measured across 0.01, 0.05, and 0.1 Pa stress each at 20° C., 25° C., and 30° C. Two separate loadings were performed to obtain the average viscosities shown in Table 4 below.

TABLE 4

| Viscosity Measurements | |
|---|---|
| Temperature (° C.) | Viscosity Pa · s |
| 20 | 1.146E−03 |
| 25 | 1.049E−03 |
| 30 | 9.831E−04 |

Animal Models and Efficacy Testing

Compositions of the present invention have been tested for their ability to inhibit growth of clinical NTM species in an acute in vivo pulmonary infection mouse model to obtain preliminary data to establish clofazimine concentration levels in lung tissue after direct respiratory delivery as opposed to systemic administration. Two separate mouse models are used in order to investigate pulmonary NTM infection, dependent on the bacterial species of interest. For testing, *Mycobacterium avium* 2285, and *Mycobacterium abscessus* 103 bacterial strains have been used (Strain details can be found in "Phylogenetic analysis of Mycobacterial species using whole genome sequences". Hazbon M. H., Riojas M. A., Damon A. M., Alalade R., Cantwell B. J., Monaco A., King S., Sohrabi A. Submitted (SEP-2014) to the EMBL/GenBank/DDBJ databases). These two species have been previously used in literature as models of NTM infection (Obregon-Henao et al. 2015 Antimicrob Agents Chemother; and Chan et al. Animal Models of Non-Tuberculous Mycobacterial Infections, Mycobact Dis 2016).

In Vivo Safety Study in Balb/C Mice

For in vivo safety and tolerability, 6-8 week old Balb/C female mice are obtained from Charles River. The mice are rested for one week before dosing. For each dose of clofazimine, three healthy mice are given a total of three doses every other day. Mice were dosed at 10.0, 5.01, and 2.51 mg/kg of clofazimine in the composition of Example 1. The compounds were given to 3 healthy mice for a total of three doses, every other day, by Microsprayer® aerosol intratracheal administration.

Clofazimine was found to be safe at 20 mg/kg (gavage, 200 µl). The composition of Example 1 showed no toxicity at the highest dose tested (10.0 mg/kg; 0.2506 mg/dose in 35 µl intratracheally). Accordingly, the composition of Formula I was considered safe and well tolerated at 10.0 mg/kg.

Determination of Minimum Inhibitory Concentration

Minimum inhibitory concentration (MIC) testing was performed by microbroth dilution method using Mueller Hinton (MH) broth (Cation Adjusted) to the calcium and magnesium ion concentration recommended in the CLSI standard M7-A7 (Becton Dickinson). MIC testing also was performed by microbroth dilution method using 7H9 broth (Sigma-Aldrich). The justification for use of both MH and 7H9 broth for compound screening is that antimycobacterial compounds have been shown to display different MIC activity depending on the broth that is used in the MIC assay.

M. abscessus was grown on 7H11 agar plates (Sigma-Aldrich) for 3 days at 35-37° C. in ambient air (depending on bacterial strain), and M. avium was grown on agar 7H11 plates (Sigma-Aldrich) for 21-30 days at 37° C. in ambient air. The colony forming units (CFUs) are taken from the agar plates and placed in either MH or 7H9 broth with 0.05% tween-80 and grown at 35-37° C. in ambient air until the optical density (OD) absorbance taken after 3 days (M. abscessus) or 12 (M. avium) of growth is an (OD) 0.08-0.1 (0.5 McFarland Standard). The bacterial cell suspensions are then confirmed by preparing them in saline, matching the (OD) 0.08-0.1 (0.5 McFarland Standard). Compound stock solutions were made by suspending the compounds in DMSO at a concentration of 1.28 mg/ml, and used immediately for test range 64-0.062 µg/ml. Following this, 180 µl of broth (either MH or 7H9) was added to the first column in the 96 well plates, and 100 µl of broth to the remaining columns in the 96 well plate. 20 µl of compound stock solution was added to the first column of wells, and serially diluted. Finally, 100 µl NTM cell suspension was added in all the wells except the media only control wells. QC agents specific for each organism 1) bacteria only negative control 2) media only negative control 3) clarithromycin positive drug controls.

M. abscessus ODs were assayed on day 3, and M. avium on day 12. Following these measurements, the plate was assayed by using the Resazurin Microtiter Assay Plate method. Briefly, the method uses the addition of resazurin (7-Hydroxy-3H-phenoxazin-3-one 10-oxide) to the 96 well plate. Resazurin is a blue dye, itself weakly fluorescent until it is irreversibly reduced to the pink colored and highly red fluorescent resorufin. It is used as an oxidation-reduction indicator to determine bacterial cell viability in MIC assays.

Assays were done in triplicate. Assay #1 was performed after storage of the Composition of Example 1 at 4° C. for 2 months, Assay #2 was performed at 4 months, and Assay #3 at five months.

Minimum Inhibitory Concentrations in the Presence and Absence of CF Sputum

Minimum inhibitory concentrations assays were performed as described above.

To investigate the effect of cystic fibrosis (CF) patient sputum on antimicrobial activity of clofazimine (CFZ) and the Composition of Example 1, sputum was collected from patients who had not received antibiotics for the previous 48 hours, and their sputum was sterilized by exposure to UV light to eliminate endogenous bacteria. Following sterilization, M. abscessus, M. avium, M. intracellulare, and M. Chimaera were incubated in 10% CF sputum before undergoing MIC testing. The MIC of the Composition of Example 1 was measured following the same CLSI protocol as described above, in the presence and absence of cystic fibrosis patient sputum. All studies were performed in duplicate.

MIC values of clofazimine and the Composition of Example 1 in the presence and absence of sputum are shown in Table 5.

TABLE 5

| Species | Identification Number | CFZ (µg/ml) | Composition of Ex. 1 (µg/ml) | CFZ + SP (µg/ml) | Composition of Ex. 1 + SP (µg/ml) |
|---|---|---|---|---|---|
| M. avium | ATCC 700898 | 0.25 | 0.125 | >2 | >2 |
| M. intracellulare | DSM 43223 | 1 | 0.125 | >2 | >2 |
| M. Chimaera | CIP 107892 | 0.5 | 0.125 | >2 | >2 |
| M. avium | B18101968 | 0.5 | 0.125 | >2 | >2 |
| M. abscessus | CIP104536 | 0.25 | 0.125 | >2 | >2 |
| M. abscessus | B18104072 | 1 | 0.25 | >2 | >2 |
| M. abscessus | B15029863 | 2 | 2 | >2 | >2 |
| M. abscessus | B12052284 | 2 | 0.5 | >2 | >2 |

The results presented in Table 5 indicate consistent MICs of both clofazimine and the Composition of Example 1, against a range of nontuberculous mycobacterial species.

These data indicate that the Composition of Example 1 demonstrates potent in vitro activity against both M. abscessus and M. avium, and is stable at least over this time period.

Mouse Model of M. abscessus in the SCID Mouse 6-8 week old SCID female mice were ordered from Charles River. Mice were rested one week before infection.

Working stocks of M. abscessus strain 103 were frozen in 1 ml aliquots and stored at −80° C. before use. For infection an aliquot was thawed, disrupted 20 times with a 1 ml luer-lok syringe fitted with a 26 g needle, and diluted in sterile 1×PBS.

The acute SCID mouse model received a non-invasive intratracheal instillation pulmonary infection with $1 \times 10^6$ CFU/mouse (M. abscessus strain 103).

Three mice were sacrificed day 1 post-infection to determine bacterial uptake. Whole lungs, spleens, and livers are extracted, homogenized in 4.5 ml of 1×PBS. Homogenates were serially diluted in 1:10 dilutions and dilutions (0-1-2-3-4-5-6-7) plated on 7H11 agar plates. The plates are placed in 32° C. dry-air incubator (strain dependent) for 7 days.

The Composition of Example 1 10.0 mg/kg was administered by a Microsprayer® (35 µl) through the pulmonary route, and clofazimine (gavage), amikacin (subcutaneous) in a volume of 200 µl per mouse which begins day 2 post-infection and continued every other day for 8 consecutive days.

Mice were sacrificed 2 days after administration of the last dose of the compounds. Six mice of all groups (untreated control, clofazimine (gavage), composition of Example 1, and amikacin treated mice) were sacrificed and bacterial loads were determined. Plating of lung homogenate at 0-1-2-3-4-5-6-7, spleen at 0-1-2-3-4-5-6-7 and liver at 0-1-2-3-4-5-6-7.

Log 10 protection values of at least 0.60 indicate activity is statistically significant. Statistical analysis was performed by first converting CFU to logarithms, which were then evaluated by a one-way ANOVA followed by a multiple comparison analysis of variance by a one-way Tukey test (GraphPad Prism analysis software). Differences are considered significant at the 95% level of confidence.

Table 6 shows the average Logo CFU data and standard error of mean (SEM) following SCID mouse *M. abscessus* infection, where "n" is the total number of animals in group at time of sacrifice.

TABLE 6

| Group | Lung $\text{Log}_{10}$ CFU ± SEM | Spleen $\text{Log}_{10}$ CFU ± SEM | Liver $\text{Log}_{10}$ CFU ± SEM |
|---|---|---|---|
| Day 1 (Pre-treatment Control) (n = 3) | 5.08 ± 0.03 | 4.42 ± 0.04 | 5.00 ± 0.11 |
| Treatment End | | | |
| Saline Control (IT) (n = 6) | 5.51 ± 0.06 | 6.33 ± 0.85 | 6.45 ± 0.34 |
| Amikacin (SQ) 150 mg/kg (n = 6) | 3.94 ± 0.11 | 4.37 ± 0.31 | 3.07 ± 0.10 |
| Clofazimine (Oral) 20 mg/kg (n = 6) | 3.33 ± 0.17 | 3.79 ± 0.10 | 4.78 ± 0.18 |
| Composition of Example 1 (IT, aerosol) 10.0 mg/kg (n = 6) | 2.66 ± 0.28 | 3.29 ± 0.25 | 4.57 ± 0.14 |

The data in Table 6 indicate that treatment with the composition of Example 1 led to the greatest reduction in bacterial recovery in the lungs and spleen of animals infected with *M. abscessus*. This bacterial reduction was statistically improved over treatment with amikacin, or oral clofazimine.

Mouse Model of *M. avium* Infection in the Beige Mouse 6-8 week old Beige female mice were ordered from Charles River. Mice were rested one week before infection.

The acute Beige mouse model received a non-invasive aerosol exposure pulmonary infection with $1 \times 10^8$ colony forming units (CFU)/ml (*M. avium* strain 2285 rough).

Working stocks of *M. avium* strain 2285 rough were frozen in 1 ml aliquots and stored at −80° C. before use. For infection an aliquot was thawed, disrupted 20 times with a 1 ml luer-lok syringe fitted with a 26 g needle, and diluted in sterile 1× phosphate buffered saline (PBS).

Three mice were sacrificed on day 1 and day 7 post-infection to determine bacterial uptake. Whole lungs, spleens, and livers were extracted, homogenized in 4.5 ml of 1×PBS and diluted 1:10. Dilutions (0-1-2-3-4-5-6-7) are plated on 7H11/OADC, TSA and charcoal agar plates and incubated at 32° C. in a dry-air incubator (strain dependent) for 30 days.

The composition of Example 1, 10.0 mg/kg was administered by a Microsprayer® (35 µl) though the pulmonary route and clofazimine (gavage) in a volume of 200 µl per mouse which begins on day 7 post-infection and continued every other day for 10 consecutive days.

Mice were sacrificed 5 days after administration of the last dose of the compounds. Six mice of all groups (untreated control, clofazimine (gavage), and the composition of Example 1) were sacrificed and bacterial loads were determined. Plating of lung homogenate at 0-1-2-3-4-5-6-7, spleen at 0-1-2-3-4-5-6-7 and liver at 0-1-2-3-4-5-6-7.

Log 10 protection values of at least 0.60 indicate activity is statistically significant. Statistical analysis was performed by first converting CFU to logarithms, which were then evaluated by a one-way ANOVA followed by a multiple comparison analysis of variance by a one-way Tukey test (SigmaStat software program). Differences are considered significant at the 95% level of confidence.

Table 7 shows the average $\text{Log}_{10}$ CFU data following Beige mouse *M. avium* infection.

TABLE 7

| Group | Lung $\text{Log}_{10}$ CFU ± SEM | Spleen $\text{Log}_{10}$ CFU ± SEM | Liver $\text{Log}_{10}$ CFU ± SEM |
|---|---|---|---|
| Day 1 (Pre-treatment Control) (n = 3) | 4.74 ± 0.01 | 0.00 ± 0.00 | 0.00 ± 0.00 |
| Day 7 (Pre-treatment Control) (n = 3) | 5.19 ± 0.04 | 0.00 ± 0.00 | 0.00 ± 0.00 |
| Treatment End | | | |
| Saline Control (IT) (n = 6) | 5.20 ± 0.03 | 3.24 ± 0.08 | 3.63 ± 0.34 |
| Clofazimine (Oral) 20 mg/kg (n = 6) | 3.95 ± 0.03 | 3.14 ± 0.03 | 3.01 ± 0.03 |
| Composition of Example 1 (Sus.) (IT, aerosol) 10.0 mg/kg (n = 6) | 3.43 ± 0.18 | 2.93 ± 0.25 | 3.10 ± 0.02 |

The data in Table 7 indicate that treatment with the composition of Example 1 led to the greater reduction in bacterial recovery in the lungs and spleen of animals infected with *M. avium*.

Chronic Beige Mouse Model 6 to 8 week-old Beige mice were rested one week before infection. Mice received a pulmonary infection of $1 \times 10^8$ CFU of *M. avium* 2285 rough on Day 0. Three mice were sacrificed on Day 1, and six mice on Day 27 to determine bacterial uptake and pre-treatment bacterial loads. Whole lungs, spleens, and livers were extracted, homogenized in 4.5 ml of 1×PBS and plated at (0-1-2-3-4-5-6-7) dilutions on 7H11 and charcoal agar plates. The plates were placed in a 37° C. dry-air incubator for 25 to 30 days.

The remaining infected Beige mice were treated every other day, starting on Day 28, for a total of 14 treatments. Animals received one of the following treatments: Saline (Microsprayer®, 35 µl); Clofazimine (oral gavage, 20 mg/kg, 200 µl); Composition of Example 1 (IT, Microsprayer®, 10 mg/kg, 35 µl).

Mice were sacrificed on Day 57, two days after the final treatment. Plates were placed in a 37° C. dry-air incubator for 30 days.

Statistical analysis was performed by first converting CFU to logarithms, which were then evaluated by a one-way ANOVA followed by a multiple comparison analysis of variance by a one-way Tukey test. Differences are considered significant at the 95% level of confidence.

Average Logo CFU data following Beige mouse *M. avium* chronic infection are shown in Table 8

TABLE 8

| Group | Lung Log$_{10}$ CFU ± SEM | Spleen Log$_{10}$ CFU ± SEM | Liver Log$_{10}$ CFU ± SEM |
|---|---|---|---|
| Day 1 (Pre-treatment Control) (n = 3) | 5.24 ± 0.05 | 0.00 ± 0.00 | 0.00 ± 0.00 |
| Day 27 (Pre-treatment Control) (n = 6) | 6.02 ± 0.07 | 5.37 ± 0.35 | 6.52 ± 0.12 |
| Treatment End (Day 57 | | | |
| Saline Control (IT) (n = 6) | 6.40 ± 0.06 | 6.15 ± 0.16 | 6.69 ± 0.14 |
| Clofazimine (Oral) 20 mg/kg (n = 6) | 5.94 ± 0.12 | 3.08 ± 0.04 | 4.07 ± 0.04 |
| Composition of Example 1 (Sus.) (IT, aerosol) 10.0 mg/kg (n = 6) | 2.45 ± 0.09 | 4.83 ± 0.22 | 3.89 ± 0.011 |

These data suggest that clofazimine has a difficult time penetrating the granuloma-like structures formed by established, "chronic" animal NTM infection models. It appears that the composition of the present invention does not have the same issues, and is able to maintain antimycobacterial activity even after the infection has become well-established.

Effect of the Composition of Example 3 on Barrier Integrity and Inflammation Following Exposure to Pulmonary Epithelial Cells In Vitro Cell Viability Three different cell types under two in vitro conditions were used to assess pulmonary epithelial cell viability: Calu-3; A549; and hAELVi cells. Cells were either treated under "submerged conditions" (i.e. in cell culture media on Transwell™ plates) or "air-liquid interface" mimicking conditions (ALI), which had cell culture media removed from the apical side of the cells. In "submerged conditions", Calu-3 cells were exposed to three doses of the Composition of Example 3 (10%, 50%, or 100%) for four hours. To estimate cell viability, cells were stained using acridine orange/propidium iodide (AO/PI) staining to differentiate live/dead cells. Red fluorescence signaled cell death.

Macrophage Uptake

THP-1 cells were differentiated to macrophage-like cells following incubation with 124 ng/ml phorbol 12-myristate 13 acetate (PMA) for 3 days. Once the cells were matured, they were exposed to the Composition of Example 3 (diluted 1:200 in Hank's Buffered Salt Solution (HBSS)) for four hours. Cells were stained via AO/PI, as described above, to determine cell viability following exposure.

Transepithelial Electrical Resistance (TEER) Measurements

Calu-3 cells were seeded at 1×10$^5$ cells/well on a Transwell™ 3460, and left for 12 days to grow to confluence. TEER measurements were performed using an EVOM2 (World Precision Instruments, Friedberg, Germany) according to the manufacture's instructions. Following seeding, Calu-3 cells were exposed to either saline (negative control) or the Composition of Example 3 (concentrations: 20 mg/ml, 10 mg/ml, or 2 mg/ml). The cells were exposed from 2 to 4 hours, before measuring TEER.

Inflammatory Cytokine Production

Differentiated THP-1 cells (dTHP-1) were exposed to the Composition of Example 3 for 4 hours or 24 hours (1:200 HBSS dilution). HBSS exposure alone was used as a negative control, and lipopolysaccharide (LPS) (100 ng/ml) was administered as a positive control.

Following the incubation, supernatant was removed from the cells t=4 hours or 24 hours, and the pooled. An enzyme linked immunosorbent assay (ELISA) was performed on the pooled supernatant samples. Individual ELISA kits for TNF-α, IL-6, IL-8, and IL-10 were used, according to the manufacturer's instructions.

Statistical analysis was performed by one-way analysis of variance (ANOVA) followed by Tukey post-hoc test. Statistical significance was determined at a probability value <0.05.

Results

Under "submerged" conditions the Composition of Example 3 led to no visual reduction in cell viability over four-hour incubation at any of the concentrations administered.

Under "ALI" conditions, three different cell types (Calu-3, A549, and HAELVi cells) were investigated over three different time points (five hours, two days, and seven days). The was little to no cytotoxicity observed at four hours in any of the cells, or at day 2 in the Calu-3 cells. Some toxicity was seen at day 2 and day 7 in A549 cells, and day 7 in Calu-3 cells. Technical limitations did not permit quantification of cell death.

With regard to macrophage uptake, differentiated THP-1 cells were incubated at 1:200 HBSS for four hours to determine macrophage cell viability after exposure. The Composition of Example 3 did not induce cell death, but did show clofazimine uptake by the macrophages.

With regard to TEER measurements, Calu-3 cells were exposed to HBSS or three concentrations of the Composition of Example 3 for four hours, and TEER measurements were sampled at various time points throughout the exposure. A reduction in TEER of 50% compared to controls at any given time point was considered a significant loss in barrier integrity.

Exposure to the Composition of Example 3 to Calu-3 cells had no effect on barrier integrity after one-hour exposure. Exposure at 20 mg/ml led to significant (i.e. 50%) reduction after two hours. At a concentration of 10 mg/ml showed a slight reduction (i.e. 25-35%) at all time points after two hours. Exposure at 2 mg/ml did not show any reduction in barrier function over the full study duration.

Inflammatory Cytokine Production

The positive control LPS behaved as expected in this model. The Composition of Example 3 demonstrated no significant changes in cytokine at any timepoint investigated.

Results are shown in Table 9.

Cytokine Production Following dTHP-1 Cell Exposure

TABLE 9

| Treatment Group | Cytokine concentration (pg/ml) | | | |
| --- | --- | --- | --- | --- |
| | TNF-α (4 hr) | IL-8 (4 hr) | IL-10 (4 hr) | IL-6 (24 hr) |
| Control | 603.0 ± 23.0 | 398.3 ± 12.0 | 16.5± | 7.9 ± 0.3 |
| LPS | 2130.7 ± 23.0* | 2596.8 ± 84.0* | 65.1 ± 7.0* | 22.6 ± 0.7* |
| Composition of Ex. 3 | 441.9 ± 48.3 | 978.9 ± 395.4 | 18.9 ± 7.1 | 6.5 ± 1.4 |

(*p < 0.05)

In Vivo Safety and Tolerability 6-8-week-pld Balb/C female mice were given a total of three doses every other day. Mice were dosed at 10.0, 5.01, and 2.51 mg/kg using the Composition of Example 1. The composition was given via Microsprayer® aerosol intratracheal (IT) administration, at volumes of 35 μl/mouse. Following instillation, the mice were observed at 10 minutes, 1, 2 and 4 hours after dosing, and then daily afterwards.

Table 10 shows gross observations following administration. "BAR" indicates the animals were bright, active and responsive.

TABLE 10

| Treatment Group | Day 1 | Day 2 | Day 3 |
| --- | --- | --- | --- |
| Group 1 10.0 mg/kg | BAR | BAR | BAR |
| Group 2 5.01 mg/kg | BAR | BAR | BAR |
| Group 3 2.51 mg/kg | BAR | BAR | BAR |

Table 11 shows weights of the animals over the three days tested.

TABLE 11

| Mouse | Dose | Weight (grams) | | |
| --- | --- | --- | --- | --- |
| | | Day 1 | Day 2 | Day 3 |
| 1 | 10 mg/kg | 20.1 | 20.2 | 22.1 |
| 2 | " | 21 | 21.2 | 22 |
| 3 | " | 21.1 | 20.2 | 22.2 |
| 1 | 5.01 mg/kg | 22.3 | 22.3 | 23.1 |
| 2 | " | 22.1 | 22 | 23.2 |
| 3 | " | 22 | 21.9 | 23.2 |
| 1 | 2.51 mg/kg | 22 | 22 | 23.3 |
| 2 | " | 22.2 | 22.2 | 22.8 |
| 3 | " | 22.4 | 22 | 23.1 |

These data indicate that there was no statistically significant change in body weight over the three treatment days. These results indicate that compositions of the present invention are well tolerated at the doses tested.

We claim:

1. A pharmaceutical composition comprising:
   a) a therapeutically effective dose of clofazimine or a pharmaceutically acceptable derivative or salt thereof;
   b) a nonionic surfactant with an Hydrophilic-Lipophilic Balance value of greater than 10; and
   c) an aqueous liquid carrier selected from water, isotonic saline, buffered saline and aqueous electrolyte solutions wherein the clofazimine, or the pharmaceutically acceptable derivative or salt thereof, is provided in the form of particles in a suspension,
   and
   wherein the particles of clofazimine, or the pharmaceutically acceptable derivative or salt thereof, have a median size of less than 5 μm and a D90 of less than 6 μm.

2. The pharmaceutical composition according to claim 1 wherein the particles of clofazimine, or the pharmaceutically acceptable derivative or salt thereof, have a mean size of less than 2 μm and a D90 of less than 3 μm.

3. The pharmaceutical composition according to claim 1, wherein the nonionic surfactant is selected from polysorbate 20, polysorbate 60, polysorbate 80, stearyl alcohol, a polyethylene glycol derivative of hydrogenated castor oil with an Hydrophilic-Lipophilic Balance value of 14 to 16, a polyethylene glycol derivative of hydrogenated castor oil with an Hydrophilic-Lipophilic Balance value of 15 to 17, sorbitan monolaurate, sorbitan monopalmitate, sorbitan monostearate, polyoxyethylene (20) oleyl ether, polyoxyethylene (20) cetyl ether, polyoxyethylene (10) cetyl ether, polyoxyethylene (10) oleyl ether, polyoxyethylene (100) stearyl ether, polyoxyethylene (10) stearyl ether, polyoxyethylene (20) stearyl ether, polyoxyethylene (4) lauryl ether, polyoxyethylene (20) cetyl ether, polyoxyethylene (2) cetyl ether, caprylocaproyl polyoxyl-8 glyceride, polyethylene glycol (20) monostearate, polyethylene glycol (40) stearate, polyethylene glycol (100) stearate, polyethylene glycol (8) stearate, and polyoxyl 40 stearate, and mixtures thereof.

4. The pharmaceutical composition according to claim 1, wherein the non-ionic surfactant is polysorbate 80, and wherein the aqueous liquid carrier is distilled water, hypertonic saline or isotonic saline.

5. The pharmaceutical composition according to claim 4 wherein the hypertonic saline is from 1% to 7% (w/v) sodium chloride.

6. The pharmaceutical composition according to claim 4 wherein the nonionic surfactant is ultrapure polysorbate 80, and wherein the aqueous liquid carrier is isotonic saline.

7. The pharmaceutical composition according to claim 1 wherein the osmolality of the composition is in the range of 200-700 mOsm/kg.

8. The pharmaceutical composition according to claim 1 wherein the osmolality of the composition is in the range of 300-400 mOsm/kg.

9. The pharmaceutical composition according to claim 1 wherein the nonionic surfactant is in the range of 0.001% to 5% (v/v) of the total composition and the amount of clofazimine is in the range of 0.1% to 20% (w/v) of the total composition.

10. The pharmaceutical composition according to claim 1, prepared by a process comprising the billowing steps:
    (1) homogenization of a suspension of clofazimine, the nonionic surfactant and water to obtain a suspension comprising clofazimine of an appropriate particle size,
    (2) adjusting the pH of the suspension resulting from (1) to a pH of between pH 5.5 and pH 7.5, and
    (3) adjusting the sodium chloride concentration to an appropriate concentration and
    (4) adjusting the osmolality to an appropriate level.

11. The pharmaceutical composition according to claim 10 wherein the pH is adjusted to 7.4, and the sodium chloride concentration is adjusted to 154 mM odium chloride.

12. The pharmaceutical composition according to claim 10, wherein the homogenization in step (1) is carried out by high pressure homogenization, high shear homogenization, wet milling, ultrasonic homogenization, or a combination of such processes.

13. The pharmaceutical composition according to claim 10 wherein the homogenization of clofazimine is carried out in multiples steps of homogenization.

14. The pharmaceutical composition according to claim 10 wherein appropriate particle size of the clofazimine are panicles baking a mean size of less than 5 µm and 1790 less than 6 µm.

15. The pharmaceutical composition according to claim 10 wherein the appropriate particle size of the clofazimine are particles having a mean size of less than 2 µm and D90 less than 3 µm.

16. A pharmaceutical combination in the form of an aerosol for inhalation, prepared by aerosolization of the composition according to claim 1 by a nebulizing device selected from an ultrasonic nebulizer, an electron spray nebulizer, a vibrating membrane nebulizer, a jet nebulizer and a mechanical soft mist inhaler, and
    wherein the aerosol particles produced by the nebulizing device have a mass median aerodynamic diameter of 1 to 5 µm.

17. A system for use in providing antibiotic activity when treating or providing prophylaxis against a pulmonary infection caused by mycobacteria or other gram-positive bacteria, wherein the system comprises:
    1) a nebulized pharmaceutical combination comprising:
        (a) a therapeutically effective dose of clofazimine;
        (b) a nonionic surfactant with an Hydrophilic-Lipophilic Balance value of greater than 10; and
        (c) an aqueous liquid carrier selected from water, isotonic saline, buffered saline and aqueous electrolyte solutions and
    2) a nebulizer,
    wherein the clofazimine is present in the form of a suspension,
    and
    wherein the aerosol particles produced by the system have a mass median aerodynamic diameter of 1 to 5 µm.

18. A method of treatment or prophylaxis of a pulmonary infection, in a patient in need thereof, comprising administering by inhalation a composition according to claim 1.

19. The method of treatment or prophylaxis according to claim 18, wherein the infection is caused by a species of the genus *Mycobacterium* selected from nontuberculous mycobacteria and *Mycobacterium tuberculosis* complex, and a combination thereof.

20. The method of treatment or prophylaxis according to claim 19 wherein the nontuberculous *Mycobacterium* is selected from *Mycobacterium avium, Mycobacterium intracellulare, Mycobacterium abscessus, and Mycobacterium leprae*, and a combination thereof.

21. The method of treatment or prophylaxis according to claim 18 wherein the infection is an opportunistic infection, selected from MAC pulmonary disease and nontuberculous infection, in a patient with cystic fibrosis, chronic obstructive pulmonary disease or acquired immune deficiency syndrome.

22. The method of treatment or prophylaxis according to claim 21 wherein the infection is an opportunistic nontuberculous mycobacteria infection in a patient with cystic fibrosis.

23. A method of treatment or prophylaxis of a pulmonary infection caused by mycobacteria or other gram positive bacteria, in a patient in need thereof, comprising administering by inhalation a composition according to claim 1, before, simultaneously, or subsequently to the administration of an agent selected from bedaquiline, or a pharmaceutically acceptable salt of derivative thereof, cefoxitine, amikacin, clarithromycin, pyrazinamide, rifampin, moxitloxacin, levotloxaetn, and para-amino salicylate, and mixtures thereof.

24. The method of treatment or prophylaxis according to claim 23, wherein the agent is bedaquiline or amikacin.

25. The method of treatment or prophylaxis according to claim 24, wherein the agent is bedaquiline.

* * * * *

UNITED STATES PATENT AND TRADEMARK OFFICE
CERTIFICATE OF CORRECTION

PATENT NO. : 11,793,808 B2
APPLICATION NO. : 17/181448
DATED : October 24, 2023
INVENTOR(S) : Hofmann et al.

Page 1 of 1

It is certified that error appears in the above-identified patent and that said Letters Patent is hereby corrected as shown below:

In the Specification

At Column 1, Lines 6-10, "This application is a national stage application of PCT/US2019/025538, filed Apr. 3, 2019, which claims the benefit of U.S. Provisional Application No. 62/722,048, filed Aug. 23, 2018, and also claims the benefit of U.S. Provisional Application No. 62/796,322, filed Jan. 25, 2019" should be changed to --This application is a continuation of PCT/US2019/025538, filed Apr. 3, 2019, which claims the benefit of U.S. Provisional Application No. 62/722,048, filed Aug. 23, 2018, and also claims the benefit of United States Provisional Application No. 62/796,822, filed Jan. 25, 2019--

Signed and Sealed this
Twenty-seventh Day of May, 2025

Coke Morgan Stewart
*Acting Director of the United States Patent and Trademark Office*